United States Patent [19]

Balkovec

[11] Patent Number: 5,516,757
[45] Date of Patent: * May 14, 1996

[54] SEMI-SYNTHETIC LIPOPEPTIDES, COMPOSITIONS CONTAINING SAID LIPOPEPTIDES, AND METHODS OF USE

[75] Inventor: James M. Balkovec, North Plainfield, N.J.

[73] Assignee: Merck & Co., Inc., Rahway, N.J.

[*] Notice: The portion of the term of this patent subsequent to Aug. 29, 2014, has been disclaimed.

[21] Appl. No.: 307,977

[22] Filed: Sep. 16, 1994

[51] Int. Cl.$^6$ ............................. A61K 38/12; C07K 7/64
[52] U.S. Cl. ..................... 514/11; 514/9; 514/2; 530/317; 930/270; 930/DIG. 548; 930/DIG. 546
[58] Field of Search ..................... 514/11, 9, 2; 530/317; 930/270, DIG. 548, DIG. 546

[56] References Cited

U.S. PATENT DOCUMENTS

| | | | |
|---|---|---|---|
| 5,166,135 | 11/1992 | Schmatz | 514/11 |
| 5,378,804 | 1/1995 | Balkovec et al. | 530/317 |

FOREIGN PATENT DOCUMENTS

| | | |
|---|---|---|
| 851310 | 8/1977 | Belgium . |
| 0431350 | 6/1991 | European Pat. Off. . |
| 0462531 | 12/1991 | European Pat. Off. . |
| 0486011 | 5/1992 | European Pat. Off. . |
| 0539088 | 4/1993 | European Pat. Off. . |
| 0561639 | 9/1993 | European Pat. Off. . |
| 2365554 | 4/1978 | France . |

OTHER PUBLICATIONS

Zambias, Journal of Medicinal Chemistry, vol. 35, pp. 2843–2855, (1992).
Walzer, et al., Diagn. Microbiol. Infect. Dis., vol. 2, pp. 1–6, 1984.

*Primary Examiner*—Christina Y. Chan
*Assistant Examiner*—T. D. Wessendorf
*Attorney, Agent, or Firm*—Elliott Korsen; Mark R. Daniel

[57] ABSTRACT

There are disclosed novel semi-synthetic lipopeptides of the formula (Seq. ID Nos. 1–6)

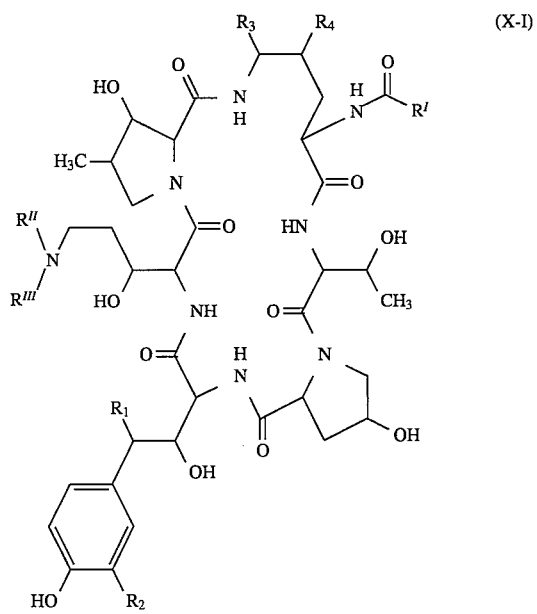

(X-I)

wherein the substituents are defined herein, which show utility as antifungal and anti-Pneumocystis agents. Pharmaceutical compositions containing said compounds are also disclosed.

5 Claims, No Drawings

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa  Thr  Xaa  Xaa  Xaa  Xaa
    1                       5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:2:

Xaa  Thr  Xaa  Xaa  Xaa  Xaa
    1                       5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:3:

Xaa  Thr  Xaa  Xaa  Xaa  Xaa
    1                       5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:4:

Xaa  Thr  Xaa  Xaa  Xaa  Xaa
    1                       5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:5:

Xaa Thr Xaa Xaa Xaa Xaa
1               5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:6:

Xaa Thr Xaa Xaa Xaa Xaa
1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:7:

Xaa Thr Xaa Xaa Xaa Xaa
1               5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:8:

Xaa Thr Xaa Xaa Xaa Xaa
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:9:

Xaa Thr Xaa Xaa Xaa Xaa
1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:10:

Xaa  Thr  Xaa  Xaa  Xaa  Xaa
1                  5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:11:

Xaa  Thr  Xaa  Xaa  Xaa  Xaa
1                  5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:12:

Xaa  Thr  Xaa  Xaa  Xaa  Xaa
1                  5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:13:

Xaa  Thr  Xaa  Xaa  Xaa  Xaa
1                  5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:14:

Xaa  Thr  Xaa  Xaa  Xaa  Xaa
1                  5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:15:

Xaa Thr Xaa Xaa Xaa Xaa
1                   5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:16:

Xaa Thr Xaa Xaa Xaa Xaa
1                   5

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:17:

Xaa Thr Xaa Xaa Xaa Xaa
1                   5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:18:

Xaa Thr Xaa Xaa Xaa Xaa
1                   5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:19:

Xaa Thr Xaa Xaa Xaa Xaa
1                   5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:20:

Xaa Thr Xaa Xaa Xaa Xaa
1               5

( 2 ) INFORMATION FOR SEQ ID NO:21:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:21:

Xaa Thr Xaa Xaa Xaa Xaa
1               5

( 2 ) INFORMATION FOR SEQ ID NO:22:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:22:

Xaa Thr Xaa Xaa Xaa Xaa
1               5

( 2 ) INFORMATION FOR SEQ ID NO:23:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:23:

Xaa Thr Xaa Xaa Xaa Xaa
1               5

( 2 ) INFORMATION FOR SEQ ID NO:24:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:24:

Xaa Thr Xaa Xaa Xaa Xaa
1               5

SEMI-SYNTHETIC LIPOPEPTIDES, COMPOSITIONS CONTAINING SAID LIPOPEPTIDES, AND METHODS OF USE

BACKGROUND OF THE INVENTION

The present invention is directed to novel cyclohexapeptidyl compounds which exhibit potent antifungal and anti-Pneumocystis activity.

There presently exists a need for new antifungal and anti-Pneumocystis compounds due to an increase in the number of isolates which are resistant to conventional agents. Additionally, conventional agents show somewhat high levels of toxicity which limit their usefulness. Lastly, the incidence of *Pneumocystis carinii* pneumonia is increasing, particularly in view of the high incidence of immunocomprised patients, such as those with AIDS.

SUMMARY OF THE INVENTION

The compounds of the present invention, Compound X (Seq ID Nos. 1–6) may be represented as (A) an amine, Compound X-I (SEQ. ID NOS. 1–6), represented by the formula:

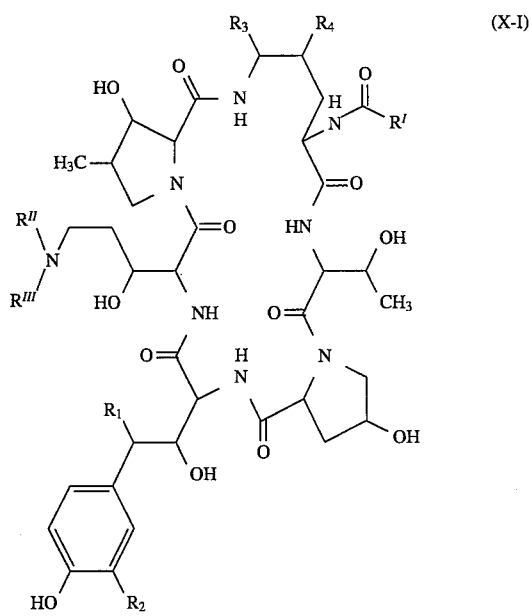

or its acid addition salt, or (B) a quaternary ammonium salt, Compound X-II (Seq. ID Nos. 1–6), represented by the formula:

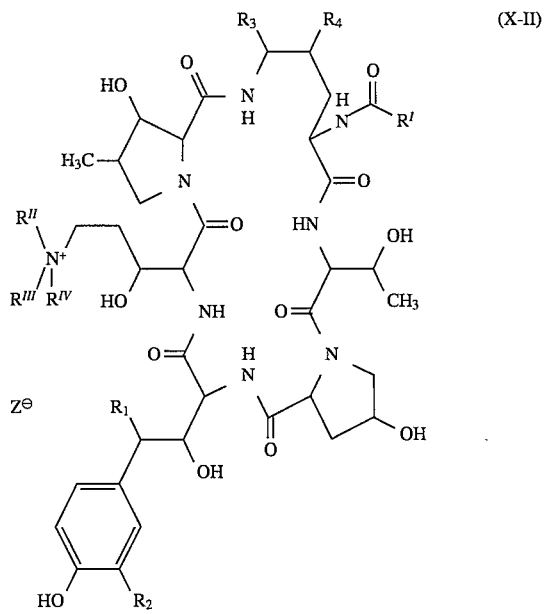

wherein
$R^1$ is H or OH,
$R^2$ is OH or $OSO_3H$ or a salt thereof,
$R^3$ is $QC_nH_{2n}NR^VR^{VI}$, $QC_nH_{2n}NR^VR^{VI}R^{VII+}Y-$,
$R^4$ is H or OH,
$R^I$ is $C_9-C_{21}$ alkyl, $C_9-C_{21}$ alkenyl, or $C_1-C_{10}$ alkoxyphenyl, or $C_1-C_{10}$ alkoxynaphthyl,
$R^{II}$ is H, $C_1-C_4$ alkyl or benzyl,
$R^{III}$ is H, $C_1-C_4$ alkyl or benzyl or $R^{II}$ and $R^{III}$ together is $-(CH_2)_4-$ or $-(CH_2)_5-$,
$R^{IV}$ is H or $C_1-C_4$ alkyl,
$R^V$ is H, $C_1-C_4$ alkyl or benzyl,
$R^{VI}$ is H, $C_1-C_4$ alkyl or benzyl or $R^V$ and $R^{VI}$ together is $-(CH_2)_4-$ or $-(CH_2)_5-$,
$R^{VII}$ is H or $C_1-C_4$ alkyl,
$R^{VIII}$ is H or $C_1-C_4$ alkyl,
Q is $NR^{VIII}$, O or S,
Y is an anion of a pharmaceutically acceptable salt,
Z is an anion of a pharmaceutically acceptable salt, and
n is 2,3 or 4.

In a preferred embodiment of this invention are compounds of the formula X-1 wherein
$R_3$ is $OCH_2CH_2NH_2$, $NHCH_2CH_2NH_2$ or $SCH_2CH_2NH_2$, and
$R^I$ is n-$C_{15}H_{31}$, p-octyloxyphenyl or 6-octyloxy-2-naphthyl.

Hereinafter, when the expression "bisamine compound" or "Compound X" is employed, it is intended to embrace the amine of formula (X-I), its acid addition salt or salts and quaternary ammonium salt of formula (X-II). "Compound X-I" will refer to the acid addition salt as well as the free base. It is to be noted that "ether", in the context of $R^3$, refers to either an oxa-ether, thioether or aza-ether. It is also to be noted that in both Compounds X-I and X-II, $R_3$ may be either an amino alkyl ether or a quaternary ammonium alkyl ether. Thus, the bisamine compound may be an uncharged compound having two amino groups or it may be a mono ammonium or a bis ammonium compound. Thus, when the "bisamine compound" is an amine, as above defined (Compound X-I) and $R_3$ is $QC_nH_{2n}NR^VR^{VI}$, the ultimate compound is uncharged and may be referred to generically as Compound X-Ia. Compound X-Ia may be represented by the following formula (Seq ID Nos. 1–6):

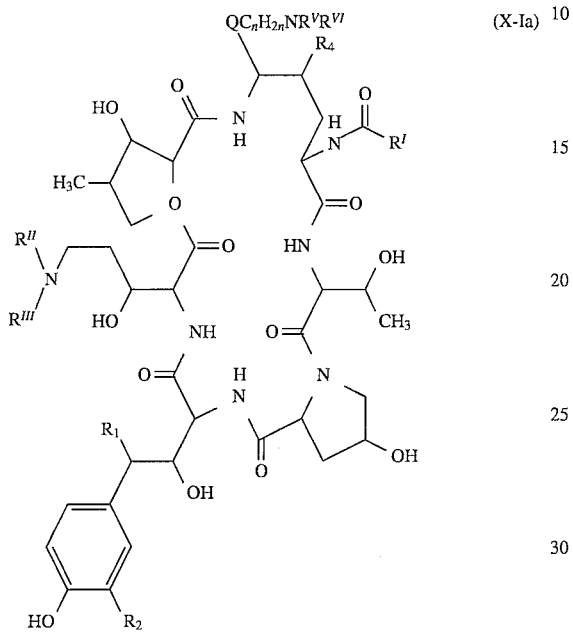

When the "amine compound" is an amine (Compound X-I) and $R_3$ is $QC_nH_{2n}NR^VR^{VI}R^{VII+}$—, the charged portion of the molecule will reside in the amino ether portion and the compound may be referred to as Compound X-Ib. Compound X-Ib may be represented by the following formula (Seq ID Nos. 1–6):

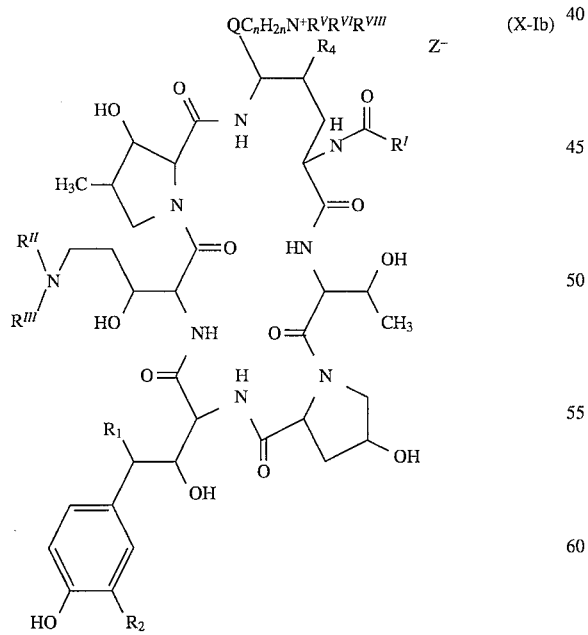

When the "amine compound" is a quaternary ammonium salt (Compound X-II) and $R_3$ is $QC_nH_{2n}NR^VR^{VI}$, the ultimate compound will be a monoquaternary ammonium salt and the compound may be referred to as Compound X-IIa.

Compound X-IIa may be represented by the following formula (Seq ID Nos. 1–6):

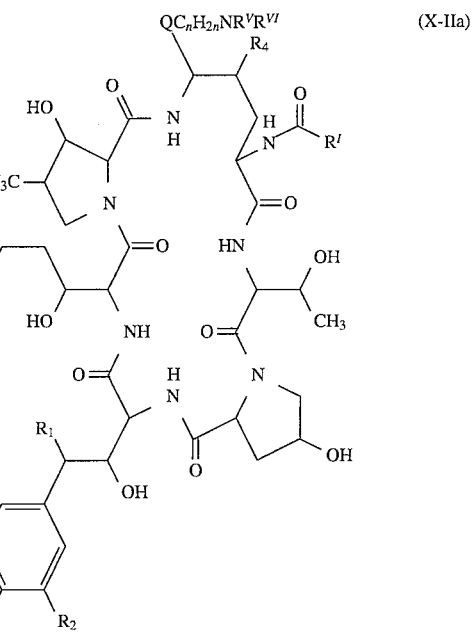

When the "mine compound" is a quaternary ammonium salt (Compound X-II) and $R_3$ is $-QC_nH_{2n}NR^VR^{VI}R^{VII}+$ $Y-$, the resulting compound will be a bis-quaternary salt and may be referred to as Compound X-IIb. Compound X-IIb may be represented by the following formula (Seq ID Nos. 1–6):

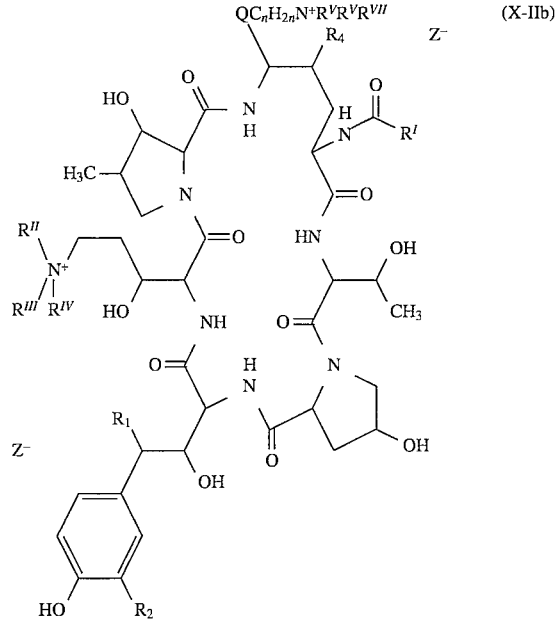

Throughout the specification and appended claims, a given chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term cycloalkyl refers to a species of alkyl containing from 3 to 15 carbon atoms without alternating or resonating double bonds between carbon atoms.

The term alkenyl refers to groups such as, e.g., vinyl, 1-propene-2-yl, 1-butene-4-yl, 4-buten-2-yl, 1-pentene-5-yl and the like.

The term alkoxy refer to straight or branched chain oxyalkyl groups such as, e.g., methoxy, ethoxy, butoxy, heptoxy, dodecyloxy, and the like.

Where the expression "ether" is employed, it is intended to include oxa-ethers, thioethers and aza-ethers as will be evident from the context. Although "aza-ethers" are technically alkylamines, for the sake of coherency, the term "aza-ether" is employed.

Representative nuclei for the bisamine compounds, Compound X, and the sequence ID for these compounds may be seen in the following table. Since the peptide nuclei would be the same irrespective of substituents $R^I$, $R^{II}$, $R^{III}$, or $R^{IV}$ and since the sequence identification number is assigned for the nuclear variations, the amines and ammonium salts have the same sequence ID's. Also, since the nucleus amino acid would be the same irrespective of the particular aminoalkyl ether, i.e., irrespective of $R^V$, $R^{VI}$ or $R^{VII}$, $R_3$ is considered to be the same for purposes of sequence identification and is not on the table. Further, since the amino acid is not varied irrespective of the change in the lipophilic side chain, separate sequence numbers are not assigned merely on the basis of a different side chain. "Lipophilic side chain" as herein employed refers to $R^I$.

| BISAMINE COMPOUND NUCLEI | $R_1$ | $R_2$ | $R_4$ | SEQ. ID NO. |
| --- | --- | --- | --- | --- |
| X-1 | OH | OSO$_3$H | OH | 1 |
| X-2 | H | OSO$_3$H | OH | 2 |
| X-3 | H | OSO$_3$H | H | 3 |
| X-4 | OH | OH | OH | 4 |
| X-5 | H | OH | OH | 5 |
| X-6 | H | OH | H | 6 |

A preferred compound X-Ia-1 is represented by the following formula:

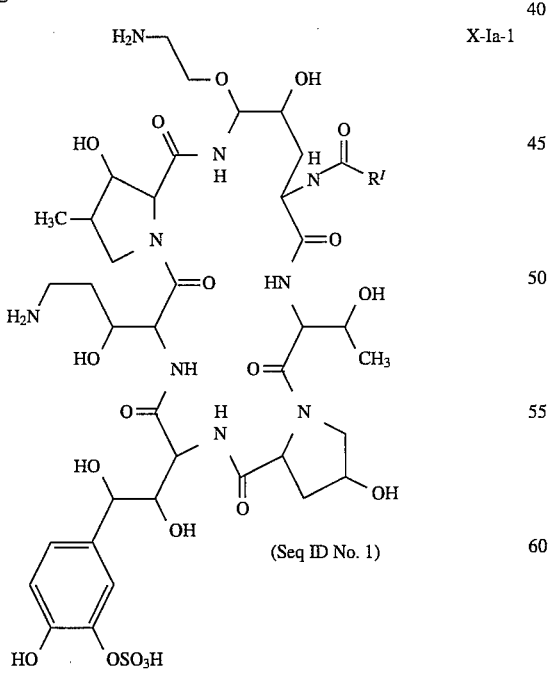

(Seq ID No. 1)

Another Preferred compound X-Ia-2 has the following formula:

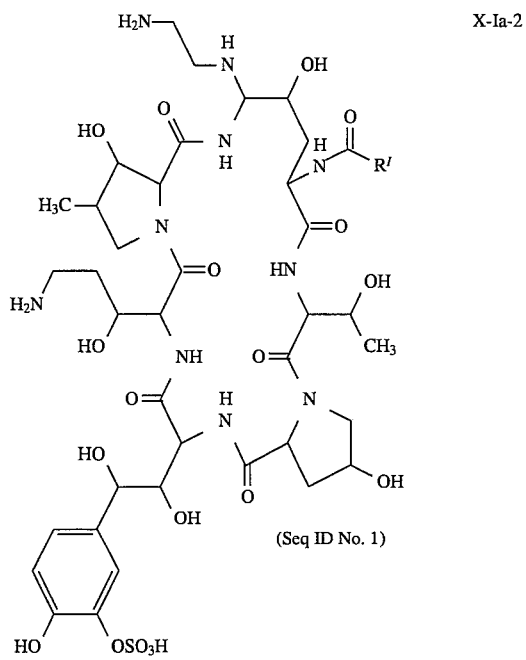

(Seq ID No. 1)

A third Preferred compound X-Ia-3 has the following formula:

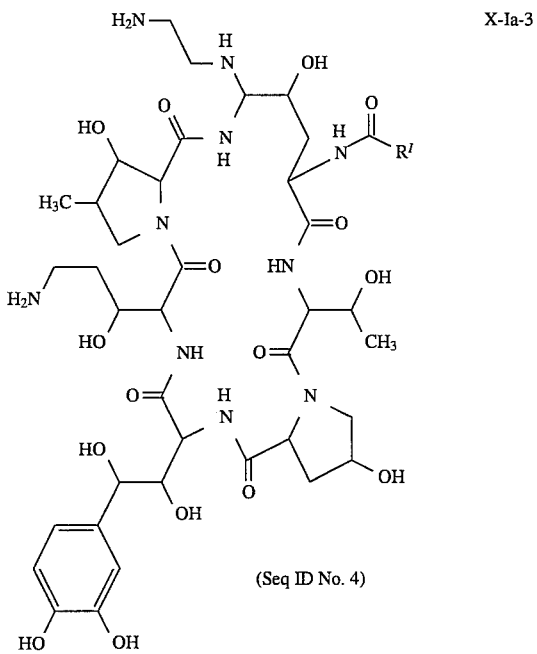

(Seq ID No. 4)

A fourth preferred compound X-Ia-4 has the following formula:

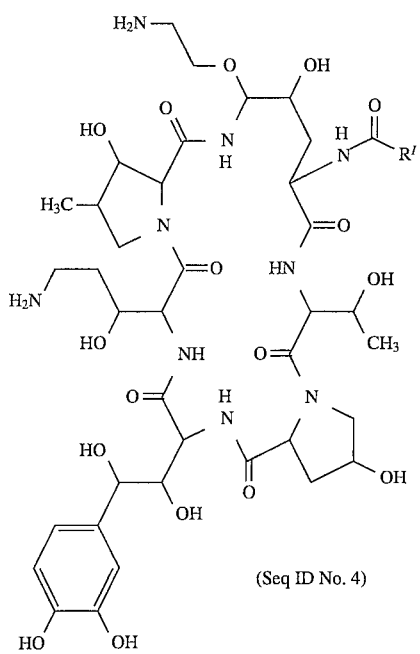

X-Ia-4

(Seq ID No. 4)

Especially preferred R' side chain groups are represented by the following formulae:

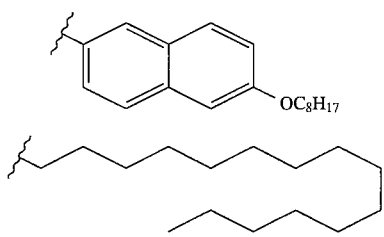

When the compounds are free amines, they are soluble in lower alcohols and polar aprotic solvents such as dimethylformamide (DMF) and pyridine. They are insoluble in solvents such as ether and acetonitrile. When the compounds are quaternary ammonium salts or protonated amines, they are soluble in water and polar solvents.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis, Cryptococcus neoformans* and Aspergillus species such as *A. fumigatus, A. flavus* and *A. niger*. They are also useful for the treatment and/or prevention of *Pneumocystis carinii* pneumonia to which immune compromised patients are especially susceptible as hereinafter described.

The previously noted solubility properties are advantageous for utilization in therapeutic applications, especially in injectible compositions.

The compounds of the present invention may be obtained from natural products or derivatives of natural products through a sequence of reactions seen in the accompanying flow diagram or from one of the intermediates which are claimed in previously filed copending applications.

The starting material represented by formula (E), which is generally a natural product but also may be a side chain derivative of a natural product and which may be obtained as hereinafter described, is first subjected to dehydration (Step A) to produce a nitrile of formula (F) which is then reduced (Step B) to an amine, which if a substituted amine is desired, may be alkylated by reductive alkylation with an appropriate aldehyde and a reducing agent such as sodium cyanoborohydride to obtain Compound G.

When Compound G has a nuclear configuration which is different from that obtained from a natural product, it may be obtained by reduction of an OH.

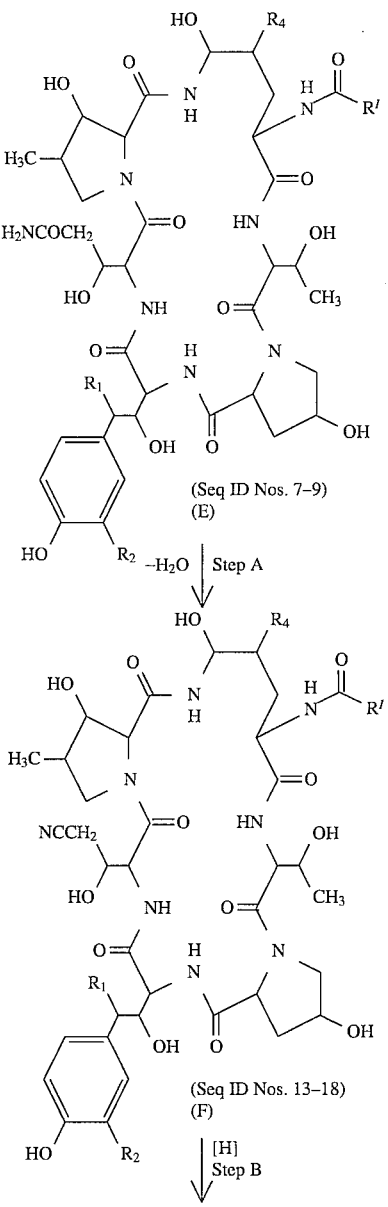

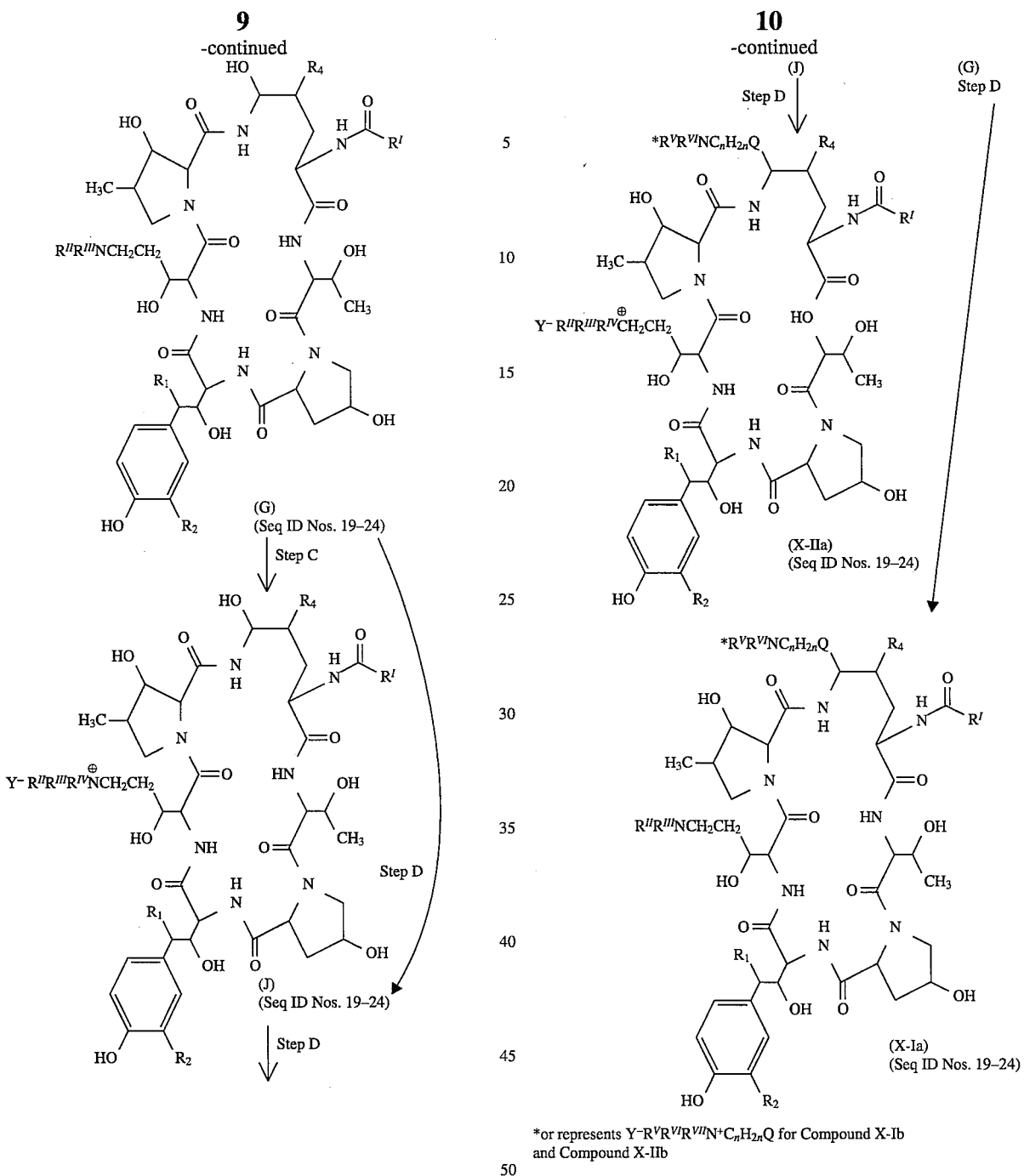

The amine may be quaternized to Compound J, by causing the amine to react with an excess alkylating agent such as alkyl halide or alkyl sulfate in the presence of a mild base such as sodium bicarbonate in an inert solvent (Step C). When all the substituents on the nitrogen are the same, the starting amine may be the primary amine (Compound G, $R^{II}$ and $R^{III}$ are H).

When Q represents "O" or "S" in Compound X, Compound G or J may be converted to the aminoalkyl ether by adding 1 to 10 equivalents of strong organic or mineral acid such as camphorsulfonic acid or hydrochloric acid to a solution of cyclohexapeptidyl propanolamine (Compound G) or the cyclohexa-peptidyl propanolammonium compound (Compound J) and 20 to 200 equivalents of the appropriate amino alcohol or aminothiol in the form of an acid addition salt, such as the hydrochloride or hydrobromide, in an appropriate solvent such as dimethylsulfoxide (DMSO) or dimethylformamide (DMF) and the mixture stirred at room temperature for one to seven days. The reaction is monitored by HPLC and when determined to be complete, the reaction mixture is diluted with 5 to 50 volumes of water and the entire mixture applied to reverse phase chromatography column. "LICHROPREP" C-18 (E. Merck) column is representative of an appropriate column. The column is then eluted with a weakly eluting solvent such as 5 percent acetonitrile in water (containing 0.1 percent trifluoroacetic (TFA) acid or acetic acid) to remove excess amino-alcohol or aminothiol, then with a stronger eluting solvent such as 10 to 50 percent acetonitrile to elute the product. Fractions containing the desired amine compound may be combined and concentrated to isolate the acid addition salt, Compound X-IIa or X-Ia, according to Steps D or D' respectively.

Compound G or J may be converted to Compound X-IIb or Compound X-Ib in a similar manner by adding 1–10 equivalents of a strong organic or mineral acid to a stirred solution of cyclohexapeptidyl propanolamine or cyclohexapeptidyl propanolammonium salt and 20 to 200 equivalents of the appropriate alkylammonium alcohol or thiol in an appropriate solvent such as DMSO or DMF, and the mixture stirred at room temperature for one to seven days until substantial completion of the reaction as can be determined by HPLC. The reaction mixture is then diluted with 5 to 50 volumes of water and the entire mixture applied to a reverse phase chromatography column. The column then may be eluted with a weakly eluting solvent such as 5 percent acetonitrile to remove excess amino alcohol or thiol and then with 10 to 50 percent acetonitrile to elute the product X-Ib or X-IIb.

When Q in Compound X represents an "NH", the following flow diagram illustrates the preparation of such compounds. Compound G or J may be converted to Compound X-IIa or Compound X-1a according to Step E where the substituent at the 5-position of the 4-hydroxyornithine is an aminoalkyl thioether, $SC_nH_{2n}NH_2$. This is accomplished in the manner outlined above for the preparation of Compound X-Ia or Compound X-IIa. The isolated aminoalkyl thioether is subjected to oxidation (Step F) with an agent such as OXONE® or meta-chloroperoxybenzoic acid in acetonitrile/water mixture as solvent. Other suitable reagents known to those skilled in the art to effect the oxidation of a thioether to a sulfone are acceptable. The compound may be purified by reverse phase chromatography or simply isolated by lyophilization of the acetonitrile/water mixture. Next, the sulfone product is contacted with a mono- or di-alkyl aminoalkylamine which may be either used as the solvent or dissolved in DMF or DMSO as solvent for a time sufficient to effect displacement of the sulfone group to give the aza-ether product according to Step G. The reaction mixture is then diluted with 5 to 50 volumes of water and the entire mixture applied to a reverse phase chromatography column. The column then may be eluted with a weakly eluting solvent such as 5 percent acetonitrile to remove excess amino alcohol or thiol and then with 10 to 50 percent acetonitrile to elute the product X-Ia, X-IIa, X-Ib or X-IIb.

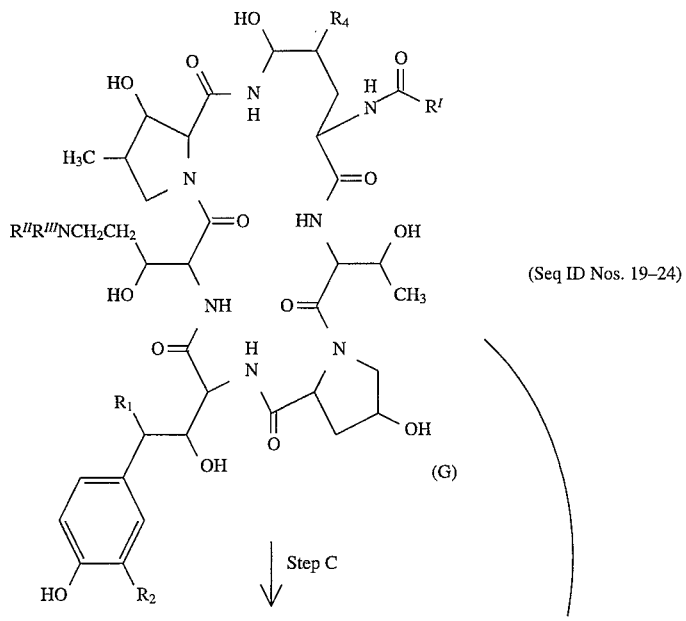

(Seq ID Nos. 19–24)

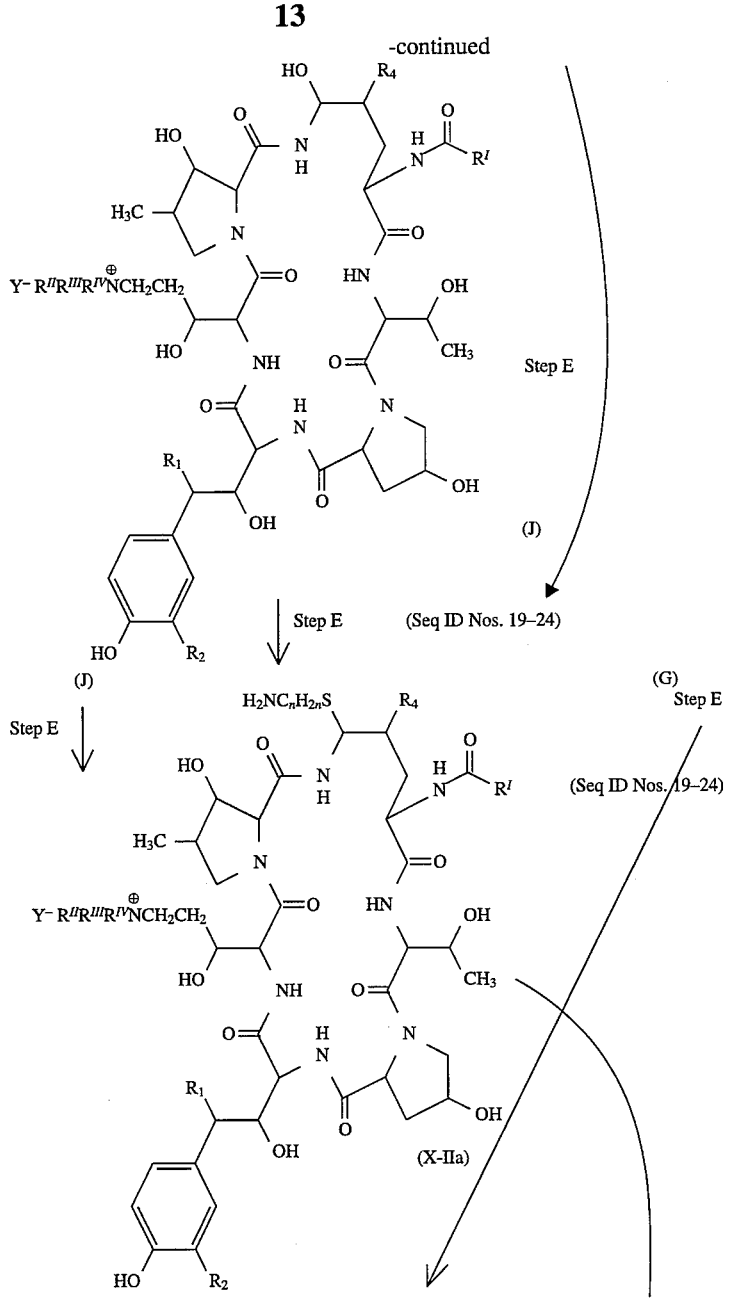

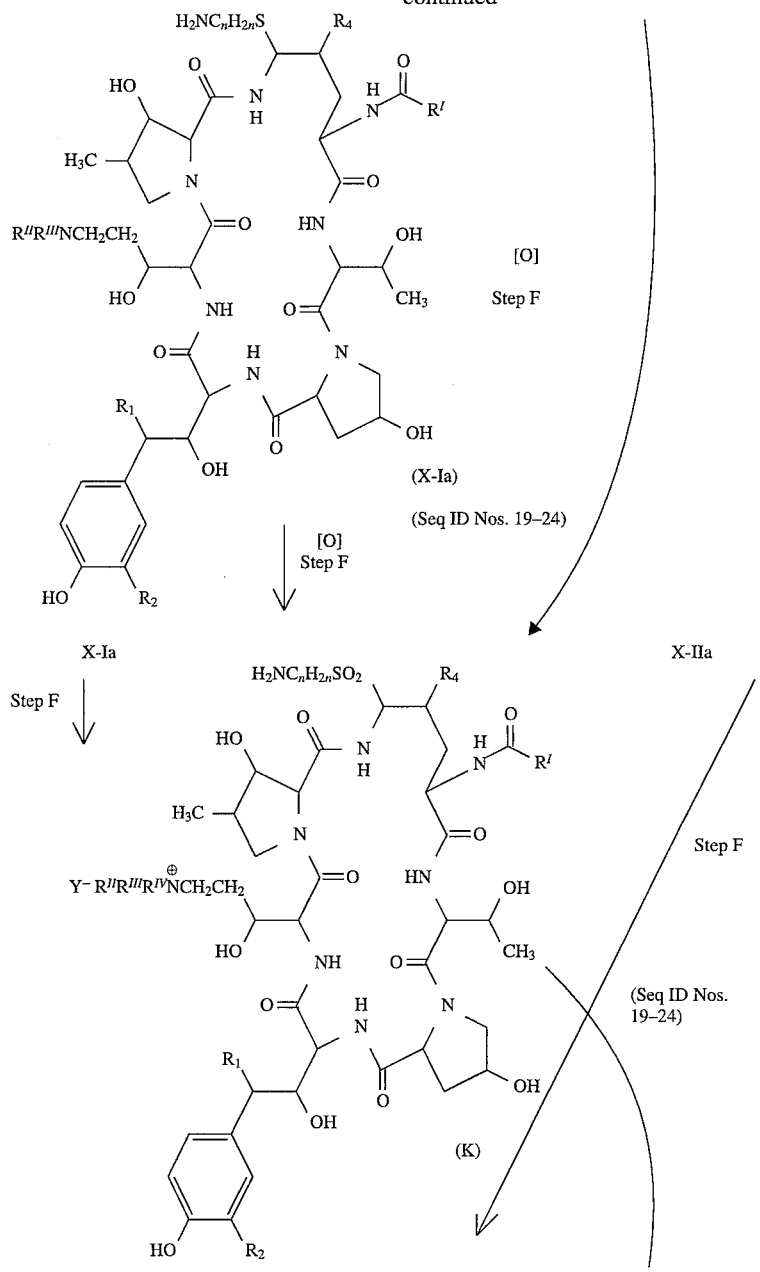

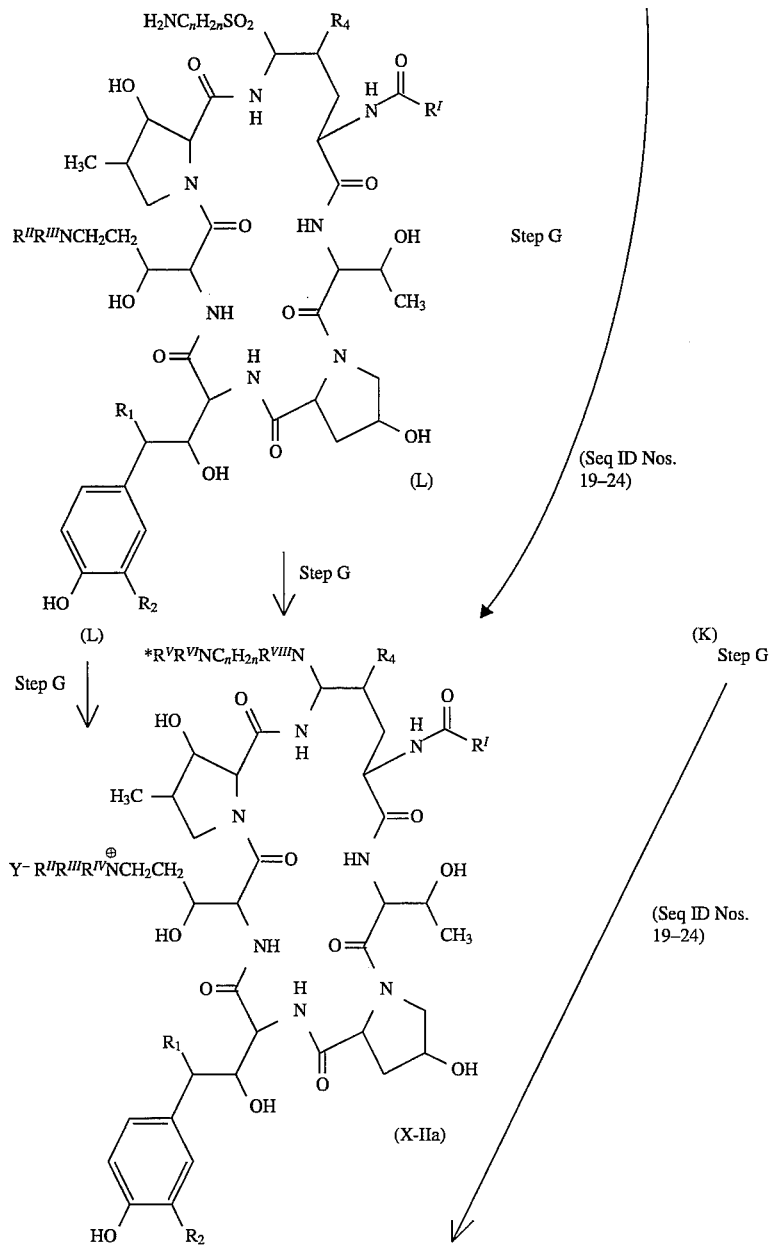

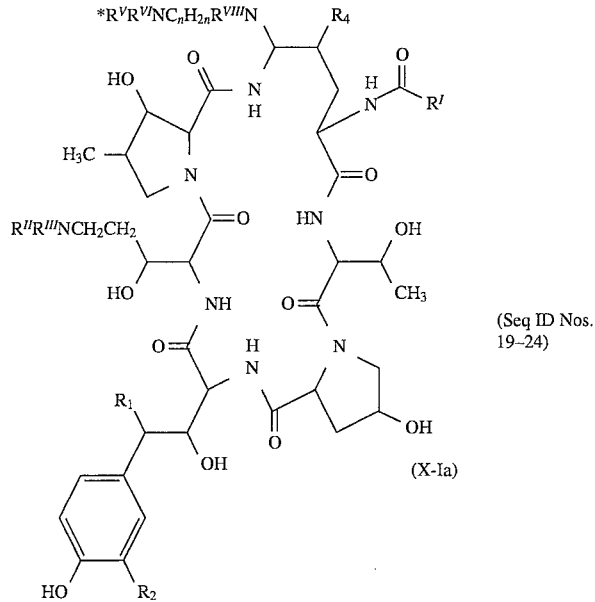

(Seq ID Nos. 19–24)

(X-Ia)

*or represents $Y^-R^VR^{VI}R^{VII}N^+C_nH_{2n}R^{VIII}N$ for Compound X-Ib and Compound X-IIb As can be seen from the foregoing flow diagrams, the amino acids in the nucleus remain the same except at the hydroxyglutamine. The aminoalkyl ethers giving rise to compounds which may be identified as bis amines are derivatives which do not change the nature of the amino acids. The sequence identification of the amines or ammonium compounds (at the original hydroxyglutamine) from which the aminoalkyl ethers, thioethers or aza-ethers are made would be the same since the amine and hydroxy group of the amino acid remain unchanged. The sequence identification of the starting material and nitrile intermediate are given below.

The sequence identification of the starting materials for the dehydration step are:

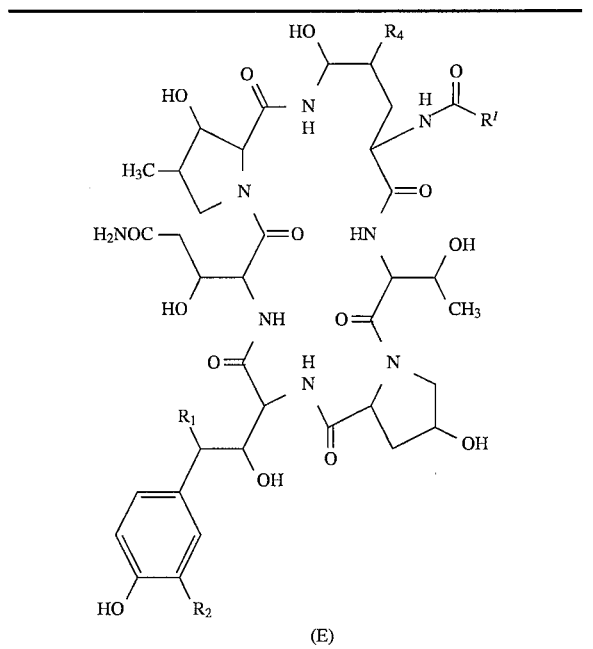

(E)

| STARTING COMPOUND | $R_1$ | $R_2$ | $R_4$ | SEQ. ID NO. |
|---|---|---|---|---|
| E-1 | OH | $OSO_3H$ | OH | 7 |
| E-2 | H | $OSO_3H$ | OH | 8 |
| E-3 | H | $OSO_3H$ | H | 9 |
| E-4 | OH | OH | OH | 10 |
| E-5 | H | OH | OH | 11 |
| E-6 | H | OH | H | 12 |

The sequence identification of the nitriles are:

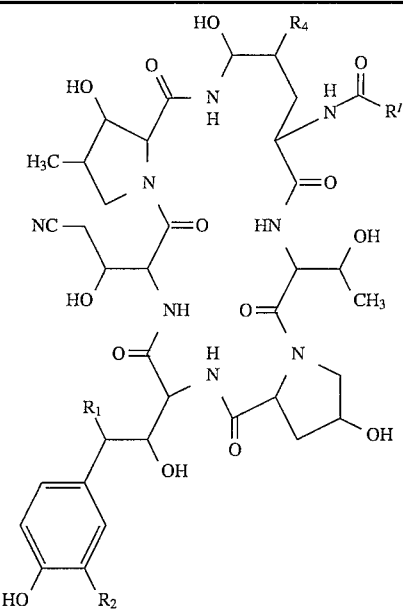

(F)

| NITRILE COMPOUND | $R_1$ | $R_2$ | $R_4$ | SEQ. ID NO. |

|       |    |                   |    |    |
|-------|----|-------------------|----|----|
| F-1   | OH | OSO$_3$H          | OH | 13 |
| F-2   | H  | OSO$_3$H          | OH | 14 |
| F-3   | H  | OSO$_3$H          | H  | 15 |
| F-4   | OH | OH                | OH | 16 |
| F-5   | H  | OH                | OH | 17 |
| F-6   | H  | OH                | H  | 18 |

The sequence identification of the propanolamines or the quaternary salts are:

| PROPANOLAMINE/ PROPANOLAMMONIUM COMPOUND | R$_1$ | R$_2$ | R$_4$ | SEQ. ID NO. |
|---|---|---|---|---|
| G/J-1 | OH | OSO$_3$H | OH | 19 |
| G/J-2 | H  | OSO$_3$H | OH | 20 |
| G/J-3 | H  | OSO$_3$H | H  | 21 |
| G/J-4 | OH | OH       | OH | 22 |
| G/J-5 | H  | OH       | OH | 23 |
| G/J-6 | H  | OH       | H  | 24 |

The first step in the preparation of Compound X-I (Seq. ID Nos. 1–6) is the dehydration of the carboxamide group of Compound E to the nitrile of Compound F. The reaction is preferably carried out under nitrogen with cyanuric chloride in a solvent in the presence or absence of molecular sieves.

Suitable reagents which may be employed in place of cyanuric chloride are anhydrides such as acetic anhydride, trifluoroacetic anhydride and phosphorus pentoxide; acid chlorides such as oxalyl chloride, phosphorus oxychloride, thionyl chloride, p-toluenesulfonyl chloride and chlorosulfonyl isocyanate; phosphonium reagents such as phosphorus pentachloride, triphenylphosphine/carbon tetrachloride, triphenylphosphonium ditriflate and triphenylphosphonium dichloride; carbodiimides such as dicyclohexylcarbodiimide; other dehydrating agents such as aluminum chloride, titanium tetrachloride, ethyl(carboxysulfamoyl)triethyl-ammonium hydroxide inner salt.

Suitable solvents include dimethylformamide or weakly basic solvents such as pyridine, collidine and the like.

Molecular sieves may be in the size range 3A to 5A.

The relative amounts of Compound E (Seq. ID Nos. 7–12) and reagents vary, but in general the dehydrating agent is used in excess. From about 1.5 to 15 equivalents of the dehydrating agent are employed. When employed the molecular sieves are used in amounts of at least tenfold by weight.

In carrying out the reaction, a suspension of molecular sieves in a rigorously dried solvent is first prepared, and while stirring under an atmosphere of nitrogen, there is added, cyanuric chloride or other dehydrating agent and thoroughly mixed. To the resulting mixture while stirring under an atmosphere of nitrogen is added the starting material, Compound E and the stirring continued for about 12 to 24 hours or until HPLC analysis of the reaction mixture indicates substantial completion of the reaction with the formation of the nitrile. When the HPLC analysis shows substantial completion of the reaction, the sieves are removed by filtration, preferably on a sintered glass funnel, and the filtrate concentrated and purified by preparative HPLC. The mobile phase used in the purification are varying ratios of a water/acetonitrile composition and an acetonitrile/water composition. These compositions are referred to in the examples as A and B. Composition A is 95/5 water/acetonitrile containing 0.1% trifluoroacetic acid (TFA) or acetic acid. Composition B is 95/5 acetonitrile/water containing 0.1% TFA or acetic acid. The exact mobile phase used for HPLC assays and the mobile phase used in preparative HPLCs may differ not only from each other but also from compound to compound, but can be determined by the skilled artisan without difficulty.

In carrying out the reaction in the absence of sieves, solid cyanuric chloride is added in a single portion to a solution of Compound E in an aprotic solvent and stirred rapidly for a short time and the reaction mixture then quenched by adding aqueous sodium acetate directly to the reaction mixture. The volatiles are then removed in vacuo to obtain a solid residue which may be purified as above described.

The reduction of the nitrile to the amine may be carried out employing either chemical or catalytic reduction. Sodium borohydride with cobaltous chloride in alcoholic solvent has been found to be particularly useful. When this combination of reagents is used, from about 5 to 50 molar equivalent of sodium borohydride and from 2 to 10 molar equivalents of cobaltous chloride are used for each molar amount of the nitrile.

Other hydride reducing agents such as sodium cyanoborohydride, aluminum hydride, diborane, diisobutyl aluminum hydride and the like also may be used. Frequently these reducing agents are used in combination with a Lewis acid such as cobaltous chloride or aluminum chloride as in the present combination of sodium borohydride and cobaltous chloride.

Catalytic hydrogenation also may be carried out over a variety of catalysts including palladium on carbon, platinum oxide, or rhodium on alumina.

Typical solvents depending on the reagent include alcohols, especially methanol and ethanol, dimethylformamide, pyridine, tetrahydrofuran or other ethers.

When the reduction of the nitrile to the amine is carried out using the preferred chemical procedure, the reaction may be carried out by adding the chemical reducing agent to the nitrile in an alcoholic solution under an atmosphere of nitrogen, and stirring until HPLC analysis using detection by ultraviolet absorption at 210 nm shows substantial completion of the reaction. When sodium borohydride is used in combination with cobaltous chloride, cobaltous chloride is added while stirring to a solution in methanol, or other solvent, of the nitrile, prepared as above described, at ambient temperature, followed by portionwise addition of the sodium borohydride which is accompanied by gas evolution. Stirring is continued for from 12 to 24 hours. The mixture may be quenched with acetic or hydrochloric at this time. Then the mixture is diluted with a highly aqueous mobile phase, 70/30 to 50/50 A:B, may be acidified with acetic acid or hydrochloric acid, filtered and purified by chromatography. The eluate fractions are lyophilized to obtain the amine as an acetic acid, trifluoroacetic acid or hydrochloric acid addition salt.

The N-alkylated or benzylated compounds may be prepared using any suitable known procedure for preparing secondary or tertiary amines. The N-benzyl compound is best prepared by first preparing a Schiff base with benzaldehyde and thereafter reducing with conventional reducing agents such as those previously noted in connection with the reduction of the nitrile although milder reducing agents may be employed.

When the desired alkyl group on the nitrogen is methyl, the carbon may be introduced by formylating, followed by reduction of the hydroxymethyl group with sodium cyanoborohydride or other reducing agent. When the desired alkyl group on the nitrogen is a higher alkyl, a preferred procedure is a reductive alkylation of an N-benzyl derivative with an aldehyde and a reducing agent such as sodium cyanoborohydride, and purifying the product with reverse phase chromatography to obtain a benzyl and a higher alkyl substituted tertiary amine. The benzyl group may be removed by hydrogenation using palladium on carbon or other suitable catalyst.

When the alkyl groups are the same, the same general procedure is preferably employed. Although alkyl halide or sulfate may be employed, these are best for quaternary salts.

When a quaternary ammonium salt is to be prepared, the appropriate amine prepared as above described is caused to react with an alkylating agent such as alkyl iodide, other alkyl halide, or alkyl sulfate in the presence of sodium bicarbonate in an inert solvent. A slight molar excess of sodium bicarbonate is employed. The alkylating agent is used in large molar excess. About six to tenfold molar excess may be employed.

When all substituents on the nitrogen are the same, the starting amine may be the primary amine. For mixed amines, it is preferable to enter the specific groups first since alkylation using an alkylating agent is more difficult to control.

To prepare the aminoalkyl ethers and thioethers, camphorsulfonic acid is added to the solution containing cyclohexapeptidyl propanolamine compound (Compound G), the appropriate aminoalkanol or aminoalkylthiol hydrochloride salt or N-carbobenzyloxy (CBZ) protected aminoalkanol or aminoalkylthiol and camphorsulfonic acid or hydrogen chloride are mixed together and the mixture allowed to stir at room temperature for one to seven days. The progress of the reaction is conveniently monitored by HPLC using acetonitrile/water as the eluting agent. After the reaction is substantially complete, the reaction mixture is diluted with water and the resulting solution applied to a reverse phase flash silica gel column and eluted with an appropriate mixture of acetonitrile and water to obtain the desired bisamine compound, or the CBZ protected bisamine compound. In the case of the latter, the protective CBZ group is removed by hydrogenolysis.

Although other alkylating agents such as substituted or protected aminoalkyl halides or sulfates (for substituted or free aminoalkyl ethers) may be employed the salt of the free base in the presence of camphorsulfonic acid or hydrogen chloride has been found to be most effective and convenient.

A large excess of the aminoalkanol or aminoalkylthiol is employed, preferably of the order of one-hundred molar equivalents. The amount of camphorsulfonic acid or hydrogen chloride is about two moles for every mole of the cyclohexapeptidyl propanolamine. The reaction medium is a suitable aprotic solvent such as dimethylsulfoxide (DMSO) or dimethylformamide (DMF) or dioxane, or combinations thereof.

For monitoring the progress of the reaction, an analytical "ZORBAX" (DuPont) column with 10 to 50 percent aqueous acetonitrile containing 0.1 percent trifluoroacetic acid (TFA) or acetic acid is suitable. For preparative purification, a reverse phase column such as "LICHROPREP" C18 of particle size 40–63 microns with 5–15 percent aqueous acetonitrile to remove solvent and 10 to 50 percent acetonitrile (containing 0.1% TFA or acetic acid) to elute the product is useful.

To prepare the aminoalkyl aza-ethers, the starting material is an aminoalkyl thioether prepared as described above.

When it is desired that both the propanolamine portion of the molecule and the aminoether, amino aza-ether or aminothioether portion of the molecule be in the quaternary ammonium form, conventional alkylating agents may be employed either on the unsubstituted amino ether or thioether or on a substituted ammonium ether or thioether. When the ether is an unsubstituted amino ether, generally, the alkylammonium group will be a trialkylammonium group in which all alkyls will be the same. If mixed substitution is desired on the amino group, alkylation of a substituted aminoalkyl ether is carried out to obtain the quaterary ammonium ether compound.

The compounds of the present invention are useful per se and in their pharmaceutically acceptable salt and hydrate forms in the treatment of fungal and Pneumocystis infections in animal and human subjects. The term "pharmaceutically acceptable salt and hydrate," refers to those salts and hydrated forms of the compounds of the present invention which would be apparent to the pharmaceutical chemist. i.e., those which are substantially non-toxic and which may favorably effect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carders. Thus, the present invention is concerned with pharmaceutical compositions and methods of treating infections utilizing as an active ingredient the novel cyclic peptide compounds.

The pharmaceutically acceptable salts referred to above also includes substantially non-toxic acid addition salts. The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

The compounds of the present invention are valuable antifungal agents active against various fungal organisms, and accordingly will likely find utility in human and veterinary medicine. The compounds of the invention are not limited to utility as medicaments; they may be used in all manner of industry, for example: additives to animal feed, preservation of food, disinfectants, and in other industrial systems where control of fungal growth is desired. For example, they may be employed in compositions in concentrations ranging from about 0.01 to about 100 parts of antibiotic per million parts of solution in order to destroy or inhibit the growth of harmful fungi on medical and dental equipment and as fungicides in industrial applications, for example in water based paints and in the white water of paper mills to inhibit the growth of harmful fungi.

In vitro antifungal activity determined in accordance with the protocol set forth below is predictive of in vivo activity, when the compounds are administered to a mammal infected with a susceptible fungal organism.

The compounds of the present invention are active against many fungi and particularly against Candida, Aspergillus and Cryptococcus species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1 percent dextrose (YNBD).

In a representative assay, Compound X-1:a-2 is solubilized in 100 percent dimethyl sulfoxide (DMSO) at an initial concentration of 5 mg/ml. Once dissolved, the drug stock is brought to a concentration of 512 mcg/ml by dilution in water such that the final DMSO concentration is about 10 percent. The solution is dispensed via a multichannel pipette into the first column of a 96-well plate (each well containing 0.075 ml of YNBD), resulting in a drug concentration of 256 mcg/ml. Compounds in the first column are diluted 2-fold across the rows yielding final drug concentrations ranging from 256 mcg/ml to 0.12 mcg/ml.

Four hour broth cultures of organisms to be tested are adjusted using a spectrophotometer at 600 nm to equal a 0.5 McFarland Standard. This suspension is diluted 1:100 in YNBD to yield a cell concentration of $1-5\times10^4$ colony forming units (CFU) per ml.

Aliquots of the suspension (0.075 ml) are inoculated into each well of the microtiter plate resulting in a final cell inoculum of $5-25\times10^3$ CFU/ml and final drug concentrations ranging from 128 mcg/ml to 0.06 mcg/ml. Each assay includes one row for drug-free control wells and one row for cell-free control wells.

After 24 hours of incubation, the microtiter plates are gently shaken on a shaker to resuspend the cells. The MIC-2000 inoculator is used to transfer a 1.5 microliter sample from each well of the 96-well microtiter plate to a single reservoir inoculum plate containing Sabouraud dextrose agar (SDA). The inoculated SDA plates are incubated for 24 hours at 35° C. However, for *Cryptococcus neoformans* strains, SDA plates are inoculated at 48 hours after being spotted on SDA before making minimum fungicidal concentration (MFC) readings.

The compounds also show in vivo effectiveness against fungi which can be demonstrated as follows:

Growth from an overnight SDA culture of *Candida albicans* MY 1055 is suspended in sterile saline and the cell concentration determined by hemocytometer count and the cell suspension adjusted to $3.75\times10^5$ cells/mi. 0.2 ml of this suspension is administered I.V. in the tail vein of mice so that the final inoculum is $7.5\times10^4$ cells/mouse. The assay is then carried out by administering aqueous solutions of the compounds at various concentrations intraperitoneally (I.P.) twice daily (b.i.d.) for four consecutive days to 18–20 gram female DBA/2 mice, which previously had been infected with *Candida albicans* in the manner described above. Distilled water is administered I.P. to *C. albicans* challenged mice as controls. After seven days, the mice are sacrificed by carbon dioxide gas, paired kidneys are removed aseptically and placed in sterile polyethylene bags containing 5 mls of sterile saline. The kidneys are homogenized in the bags, serially diluted in sterile saline and aliquots spread on the surface of SDA plates. The plates are incubated at 35° C. for 48 hours and yeast colonies are enumerated for determination of colony forming units per gram of kidney tissue.

The compounds of the present invention may also be used to prevent or treat *Pneumocystis carinii* infections in immunocompromised patients. *Pneumocystis carinii* may become opportunistic in mammals which are immunocompromised, such as in AIDS patients. The efficacy of the compounds for therapeutic or anti-infective purposes may be demonstrated in studies on immunosuppressed rats.

In a representative study, Sprague-Dawley rats (weighing approximately 250 grams) are immunosuppressed with dexamethasone in the drinking water (2.0 mg/L) and maintained on a low protein diet for seven weeks to induce the development of Pneumocystis pneumonia from a latent infection. Before drug treatment, two rats can be sacrificed to confirm the presence of *Pneumocystis carinii* pneumonia (PCP).

Five rats (weighing approximately 150 grams) are injected twice daily for four days subcutaneously (sc) with a compound of the invention in 0.25 ml of vehicle (water). A vehicle control is also carded out. All animals are continued on dexamethasone in the drinking water and a low protein diet during the treatment period. At the completion of the treatment, all animals are sacrificed, the lungs are removed and processed, and the extent of disease determined by microscopic analysis of stained slides.

With respect to Pneumocystis, the compounds of the invention can thus be used to treat an infection which has been diagnosed or the compound can be used in those mammalian patients who are immunocompromised and predisposed to developing a Pneumocystis infection, to prevent the organism from becoming pathogenic and causing an infection. As used herein, both treatment modalities are included in the invention.

The compounds of this invention may be used in a variety of pharmaceutical preparations. The compound may be employed in solid, powder or crystalline form, in liquid solution, or in suspension. They may be administered by a variety of means; those of principal interest include: topically, orally, parenterally by injection (intravenously or intramuscularly) and for purposes of treating Pneumocystis pneumonia, via inhalation as a powder or liquid.

Compositions for injection, one preferred route of delivery, may be prepared in unit dosage form in ampoules, or in multidose containers. The injectable compositions may take such forms as suspensions, solutions or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water.

Topical applications are also preferred for the treatment of candidiasis, and may be formulated in hydrophobic or hydrophilic bases as ointments, creams, lotions, paints, or powders.

Compositions administered orally may take such forms as tablets, capsules, oral suspensions and oral solutions. The oral compositions may utilize conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the medical arts. Another factor influencing the precise dosage regimen, apart from the nature of the infection and peculiar identity of the individual being treated, is the molecular weight of the compound.

The compositions for human use per unit dosage, whether liquid or solid, may contain from about 0.01% to as high as about 99% of active material, the preferred range being from about 10–60%. The composition will generally contain from about 1.5 mg to about 2.0 g of the active ingredient; however, in general, it is preferable to employ a dosage amount in the range of from about 1 mg to 500 mg.

In parenteral administration, the unit dosage will typically include the pure compound in sterile water solution or in the form of a soluble powder intended for solution, which can be adjusted to neutral pH and isotonic.

The preferred methods of administration of the compounds of the invention include oral and parenteral, e.g., i.v. infusion, i.v. bolus and i.m. injection.

For adults, about 0.5–50 mg of the compound per kg of body weight given one to four times daily is preferred. The preferred dosage is 2.5 mg to 1000 mg of the compound given one to four times per day. More specifically, for mild infections a dose of about 2.5 to 100 mg administered two or three times daily is recommended. For moderate infections against highly susceptible organisms a dose of about 500 mg three or four times daily is recommended. For severe, life-threatening infections against organisms at the upper limits of sensitivity to the compound, a dose of about 1000–2000 mg three to four times daily may be recommended.

For the treatment of vaginal candidiasis, the compound may be administered in a predetermined amount which is not necessarily adjusted for body weight, e.g., 50 mg given once daily for seven to ten days. Typically compounds used for the treatment of vaginal candidiasis will be formulated in a cream or suppository form which is administered intravaginally.

For the treatment of *Pneumocystis carinii* pneumonia, the compound may preferably be administered via the pulmonary route, such as through the use of an intermittent positive pressure breathing (IPPB) apparatus, or in the form of an aerosol or unit dose spray powder. Typically the compound is administered three or four times daily, in an amount sufficient to treat the infection which has developed, or to prevent the development of infection.

As used herein, prevention of a Pneumocystis infection in an immunocompromised mammalian patient involves administering a compound of the invention to the patient prior to the development of symptoms, based upon an expectation that the immunocompromised patient is more likely to develop a Pneumocystis infection than an immune competent patient. Immunocompromised patients are readily recognized by the skilled artisan by reviewing the overall condition of the patient, taking into account blood chemistry and cellular component values, e.g., the CD4 lymphocyte count.

For children, a dose of about 0.5–25 mg/kg of body weight given 2,3, or 4 times per day is preferred; a dose of about 10 mg/kg is typically recommended.

The invention is further illustrated in connection with the following non-limiting examples.

EXAMPLE I

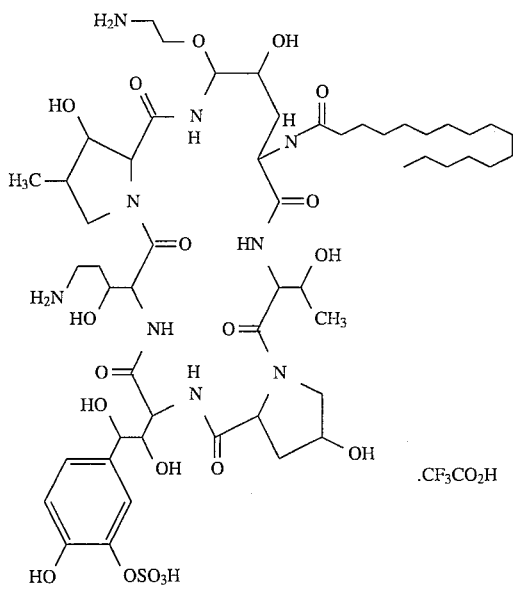

A. Preparation of Intermediate Nitrile Compound (Compound F-Ia) (Seq. ID. No. 13)

Compound E-1, which may be obtained as described in EPO 43 1350 Å, is dissolved in DMF (predried over a combination of 13X and 3 Å molecular sieves) to give a 0.04M solution. Cyanuric chloride (1.5 molar eq) is added in one portion. After approximately 5 minutes, 2M sodium acetate solution (4.6 eq) is added to quench the reaction. The DMF is removed by rotary evaporation and the residue is dissolved in a minimal amount of methanol. Purification by reverse phase chromatography (ZORBAX C18, 40% acetonitrile/60% water/0.5% $NH_4H_2PO_4$, 210 nm) and lyophilization gives a solid. The residue is dissolved in water and chromatographed (ZORBAX C18, step gradient 5% acetonitrile/95% water to 60% acetonitrile/40% water). The appropriate fractions are pooled, frozen and lyophilized to give the desired compound as the ammonium salt with a molecular weight of 1174.34.

B. Preparation of Intermediate Propanolamine G-Ia (Seq. ID No. 19)

A solution of nitrile F-1 (1 molar eq) is prepared in methanol and the reaction vessel is flushed with nitrogen. Cobalt (II) chloride hexahydrate (4.0 molar eq.) is added at room temperature to provide a purple solution. With adequate stirring, sodium borohydride (20 molar eq) is added in portions over about 15 minutes. The addition of sodium borohydride produces a black precipitate which is accompanied by gas evolution. Gas evolution accompanies each of the additions. Stirring is continued for several hours or until the reaction is judged complete by analytical HPLC. The black precipitate is dissolved by the addition of 1N HCl. The clear solution is diluted with water and applied to a preparative HPLC system for purification (ZORBAX C18, 40% acetonitrile/60% water/0.1% TFA, 210 nm). The appropriate fractions are pooled and lyophilized to obtain the desired product with a molecular weight of 1161.34.

C. Preparation of Compound X-Ia-la

The propanolamine compound prepared as above is added together with ethanolamine hydrochloride (200 equivalents) and camphorsulfonic acid (1.0 equivalent) in dry dimethylsulfoxide (DMSO) and dimethylformamide. The mixture is stirred for about one week or until reaction is complete. HPLC analysis (ZORBAX C18, 40% acetonitrile/60% water/0.5% $NH_4H_2PO_4$, 210 nm) is convenient for determining the extent of reaction. The mixture is then diluted with water and placed on a reverse phase silica gel column ("LICHROPREP" C18) packed in 85 percent water/15 percent acetonitrile. Elution with an increasing step gradient provides the product, obtained after lyophilization of the appropriate fractions. The material may be further purified by dissolving in water and chromatographing (ZORBAX C18, step gradient 5% acetonitrile/95% water/0.1% TFA to 60% acetonitrile/40% water/0.1% TFA). The appropriate fractions are pooled, frozen and lyophilized to give the desired compound as a trifluoroacetate salt with a molecular weight of 1318.44.

EXAMPLE II

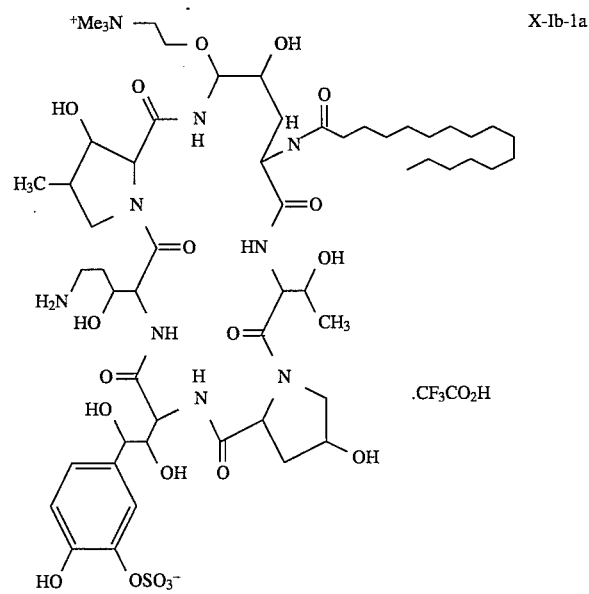

A solution of Compound G-Ia (Seq. ID No. 19) (prepared as described in Example I) and 100 equivalents of hydroxyethyl trimethylammonium chloride and 20 milligrams (2 eq) of camphorsulfonic acid is dissolved in DMSO containing a small amount of DMF. The resulting mixture is stirred at room temperature until HPLC analysis indicates conversion of the starting material. The reaction mixture is then purified by reverse phase HPLC (ZORBAX C18, 50/50 acetonitrile/water containing 0.1% TFA). Pure fractions as determined by HPLC are pooled and lyophilized to give the desired product as a trifluoroacetate salt, Compound X-Ib (Seq. ID No. 1), M.W.=1360.52.

EXAMPLE III

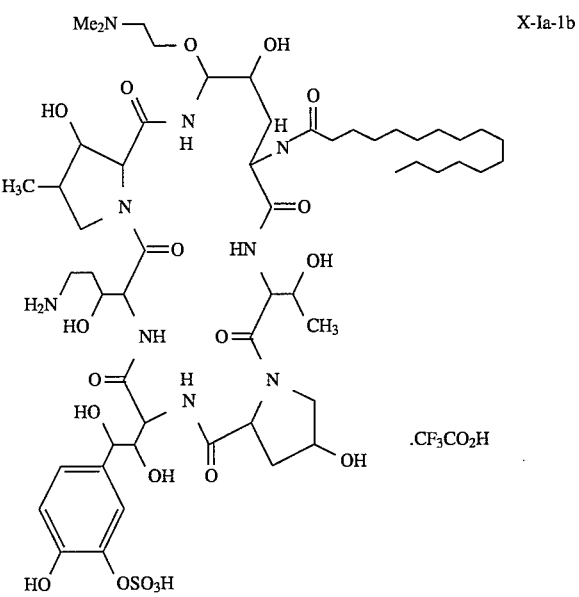

A solution of Compound G-Ia (Seq. ID No. 19) (prepared as described in Example I) and 100 equivalents of hydroxyethyl diimethylammonium chloride and 20 milligrams (2 eq) of camphorsulfonic acid is dissolved in DMSO containing a small amount of DMF. The resulting mixture is stirred at room temperature until HPLC analysis indicates conversion of the starting material. The reaction mixture is then purified by reverse phase HPLC (ZORBAX C18, 40/60 acetonitrile/water containing 0.1% TFA). Pure fractions as determined by HPLC are pooled and lyophilized to give the desired product as a trifluoroacetate salt, Compound X-Ia-3 (Seq. ID No. 1), M.W.=1346.49.

EXAMPLE IV

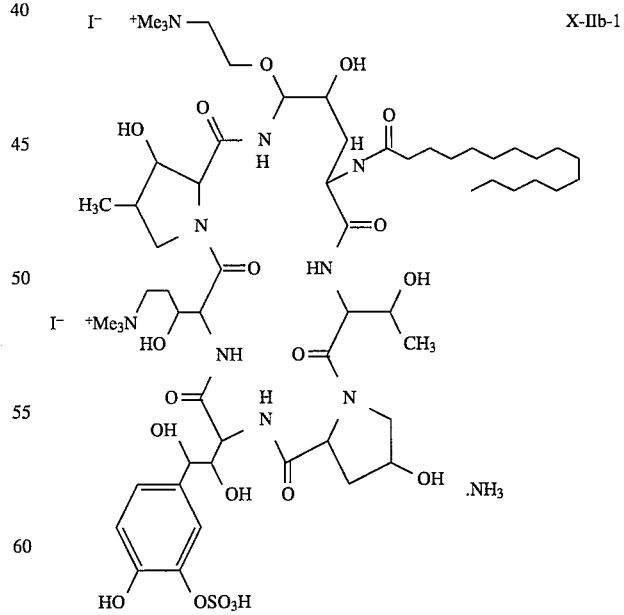

Compound X-la (1.0 molar equivalents) prepared in Example I is dissolved in dry DMF. Sodium bicarbonate (20 molar equivalents) is added followed by iodomethane (20 molar equivalents). The mixture is stirred for several hours until starting material is consumed. The volatiles are removed by rotary evaporation and the residue is diluted with water. The mixture is then purified by reverse phase HPLC (ZORBAX C18, 40/60 acetonitrile/water containing 0.1% TFA). Pure fractions of the desired product as determined by HPLC ("ZORBAX" C18, 30% acetonitrile/water/ 0.1% NH$_4$H$_2$PO$_4$) are pooled and lyophilized to give the desired product Compound as a mixed salt, X-IIb-1 (Seq. ID No. 1), M.W.=1561.43.

EXAMPLE V

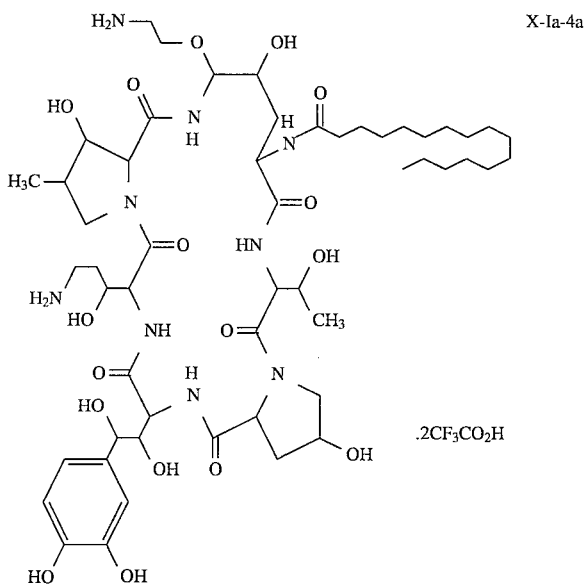

A. Preparation of Intermediate Nitrile Compound (Compound F-4a) (Seq, ID No. 16)

Compound E-4, which may be obtained as described in EPO 431350A, is dissolved in DMF (predried over a combination of 13X and 3Å molecular sieves) to give a 0.04M solution. Cyanuric chloride (1.5 molar eq) is added in one portion. After approximately 5 minutes, 2M sodium acetate solution (4.6 eq) is added to quench the reaction. The DMF is removed by rotary evaporation and the residue is dissolved in a minimal amount of methanol. Purification by reverse phase chromatography (ZORBAX C18, 40% acetonitrile/60% water, 0 nm) and lyophilization gives the desired compound with a molecular weight of 1077.25.

B. Preparation of Intermediate Propanolamine G-4a (Seq. ID No. 22)

A solution of nitrile F-4 (1 molar eq) is prepared in methanol and the reaction vessel is flushed with nitrogen. Cobalt (II) chloride hexahydrate (4.0 molar eq.) is added at room temperature to provide a purple solution. With adequate stirring, sodium borohydride (20 molar eq) is added in portions over about 15 minutes. The addition of sodium borohydride produces a black precipitate which is accompanied by gas evolution. Gas evolution accompanies each of the additions. Stirring is continued for several hours or until the reaction is judged complete by analytical HPLC ("ZORBAX" C18, 30% acetonitrile/water/0.1% TFA, 210 nm). The black precipitate is dissolved by the addition of 1N HCl. The clear solution is diluted with water and applied to a preparative HPLC system for purification (ZORBAX C18, 40% acetonitrile/60% water/0.1% TFA, 210 nm). The appropriate fractions are pooled and lyophilized to obtain the desired product as a trifluoroacetate salt with a molecular weight of 1195.31.

C. Preparation of Compound X-Ia-4a

The propanolamine compound prepared as above is added together with ethanolamine hydrochloride (200 equivalents) and camphorsulfonic acid (1.0 equivalent) in dry dimethylsulfoxide (DMSO) and dimethylformamide. The mixture is stirred for about one week or until reaction is complete. HPLC analysis (ZORBAX C18, 40% acetonitrile/60% water, 210 nm) is convenient for determining the extent of reaction. The mixture is then diluted with water and placed on a reverse phase silica gel column ("LICHROPREP" C18) packed in 85 percent water/15 percent acetonitrile. Elution with an increasing step gradient provides the product, obtained after lyophilization of the appropriate fractions. The material may be further purified by dissolving in water and chromatographing (ZORBAX C18, step gradient 5 % acetonitrile/95 % water/0.1% TFA to 40% acetonitrile/60% water/0.1% TFA). The appropriate fractions as determined by analytical HPLC ("ZORBAX" C18, 30% acetonitrile/ water/0.1% TFA, 210 nm) are pooled, frozen and lyophilized to give the desired compound as a bis-trifluoroacetate salt with a molecular weight of 1352.40.

EXAMPLE VI

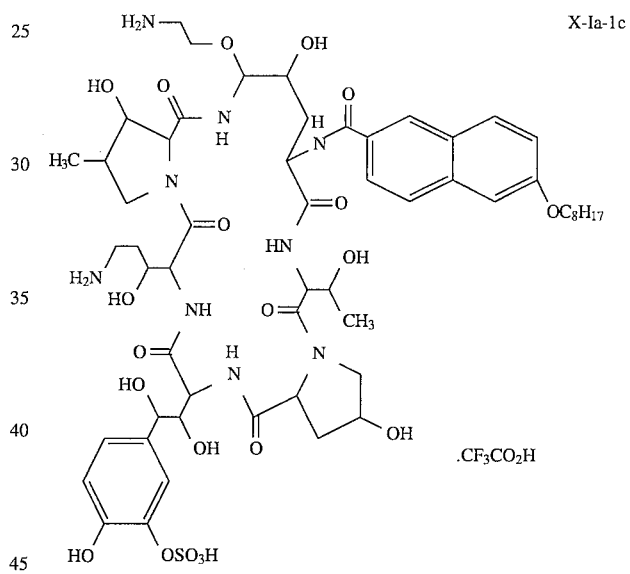

A. Preparation of Intermediate Nitrile Compound (Compound F-Ia) (Seq. ID No. 13)

Compound E-1, which may be obtained as described in EPO 46253 1A, is dissolved in DMF (predried over a combination of 13X and 3Å molecular sieves) to give a 0.04M solution. Cyanuric chloride (1.5 molar eq) is added in one portion. After approximately 5 minutes, 2M sodium acetate solution (4.6 eq) is added to quench the reaction. The DMF is removed by rotary evaporation and the residue is dissolved in a minimal amount of methanol. Purification by reverse phase chromatography (ZORBAX C18, 40% acetonitrile/60% water/0.5% NH$_4$H$_2$PO$_4$, 210 nm) and lyophilization gives a solid. The residue is dissolved in water and chromatographed (ZORBAX C 18, step gradient 5% acetonitrile/95% water to 40% acetonitrile/60% water). The appropriate fractions are pooled, frozen and lyophilized to give the desired compound as an ammonium salt with a molecular weight of 1218.31.

B. Preparation of Intermediate Propanolamine G-Ia (Seq. ID NO. 19)

A solution of nitrile F-1 (1 molar eq) is prepared in methanol and the reaction vessel is flushed with nitrogen.

Cobalt (II) chloride hexahydrate (4.0 molar eq.) is added at room temperature to provide a purple solution. With adequate stirring, sodium borohydride (20 molar eq) is added in portions over about 15 minutes. The addition of sodium borohydride produces a black precipitate which is accompanied by gas evolution. Gas evolution accompanies each of the additions. Stirring is continued for several hours or until the reaction is judged complete by analytical HPLC. The black precipitate is dissolved by the addition of 1N HCl. The clear solution is diluted with water and applied to a preparative HPLC system for purification (ZORBAX C18, 40% acetonitrile/60% water/0.1% TFA, 210 nm). The appropriate fractions are pooled and lyophilized to obtain the desired product with a molecular weight of 1205.31.

C. Preparation of Compound X-Ia-1c

The propanolamine compound prepared as above is added together with ethanolamine hydrochloride (200 equivalents) and camphorsulfonic acid (1.0 equivalent) in dry dimethylsulfoxide (DMSO) and dimethylformamide. The mixture is stirred for about one week or until reaction is complete. HPLC analysis (ZORBAX C18, 40% acetonitrile/60% water/0.5% $NH_4H_2PO_4$, 210 nm) is convenient for determining the extent of reaction. The mixture is then diluted with water and placed on a reverse phase silica gel column ("LICHROPREP" C18) packed in 85 percent water/15 percent acetonitrile. Elution with an increasing step gradient provides the product, obtained after lyophilization of the appropriate fractions. The material may be further purified by dissolving in water and chromatographing (ZORBAX C18, step gradient 5% acetonitrile/95% water/0.1% TFA to 40% acetonitrile/60% water/0.1% TFA). The appropriate fractions are pooled, frozen and lyophilized to give the desired compound as a trifluoroacetate salt with a molecular weight of 1362.41.

EXAMPLE VII

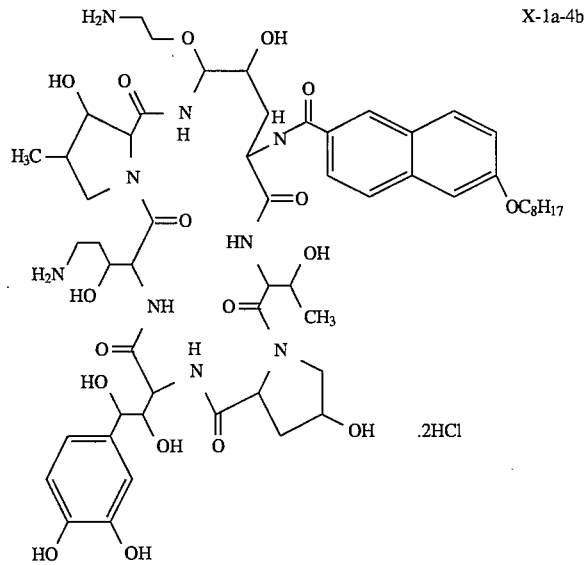

A. Preparation of Intermediate Nitrile Compound (Compound F-4a) (Seq. ID No. 16)

Compound E-4, which may be obtained as described in EPO 462531, is dissolved in DMF (predried over a combination of 13X and 3Å molecular sieves) to give a 0.04M solution. Cyanuric chloride (1.5 molar eq) is added in one portion. After approximately 5 minutes, 2M sodium acetate solution (4.6 eq) is added to quench the reaction. The DMF is removed by rotary evaporation and the residue is dissolved in a minimal amount of methanol. Purification by reverse phase chromatography (ZORBAX C18, 50% acetonitrile/50% water, 210 nm) and lyophilization gives the desired compound with a molecular weight of 1121.22.

B. Preparation of Intermediate Propanolamine G-4b (Seq. ID No, 22)

A solution of nitrile F-4 (1 molar eq) is prepared in methanol and the reaction vessel is flushed with nitrogen. Cobalt (II) chloride hexahydrate (4.0 molar eq.) is added at room temperature to provide a purple solution. With adequate stirring, sodium borohydride (20 molar eq) is added in portions over about 15 minutes. The addition of sodium borohydride produces a black precipitate which is accompanied by gas evolution. Gas evolution accompanies each of the additions. Stirring is continued for several hours or until the reaction is judged complete by analytical HPLC ("ZORBAX" C18, 30% acetonitrile/water/0.1% TFA, 210 nm). The black precipitate is dissolved by the addition of 1N HCl. The clear solution is diluted with water and applied to a preparative HPLC system for purification (ZORBAX C18, 40% acetonitrile/60% water/0.1% TFA, l=210 nm). The appropriate fractions are pooled and lyophilized to obtain the desired product as a trifluoroacetate salt with a molecular weight of 1239.27

C. Preparation of Compound X-1a-4b

The propanolamine compound prepared as above is added together with ethanolamine hydrochloride (200 equivalents) and camphorsulfonic acid (1.0 equivalent) in dry dimethylsulfoxide (DMSO) and dimethylformamide. The mixture is stirred for about one week or until reaction is complete. HPLC analysis (ZORBAX C18, 40% acetonitrile/60% water, 210 nm) is convenient for determining the extent of reaction. The mixture is then diluted with water and placed on a reverse phase silica gel column ("LICHROPREP" C18) packed in 85 percent water/15 percent acetonitrile. Elution with an increasing step gradient provides the product, obtained after lyophilization of the appropriate fractions. The material may be further purified by dissolving in water and chromatographing (ZORBAX C18, step gradient 5 % acetonitrile/95 % water/0.1% TFA to 40% acetonitrile/60% water/0.1% TFA). The appropriate fractions as determined by analytical HPLC ("ZORBAX" C18, 30% acetonitrile/ water/0.1% TFA, 210 nm) are pooled, frozen and lyophilized to give the desired compound as a bis-trifluoroacetate salt with a molecular weight of 1396.37. The compound is converted to the dihydrochloride salt by passing through a Bio-Rad AG2-X8 (Cl⁻) polyprep column washing with additional water. The product-containing eluate is lyophilized to give the desired product as the dihydrochloride salt with a molecular weight of 1241.24.

EXAMPLE VIII

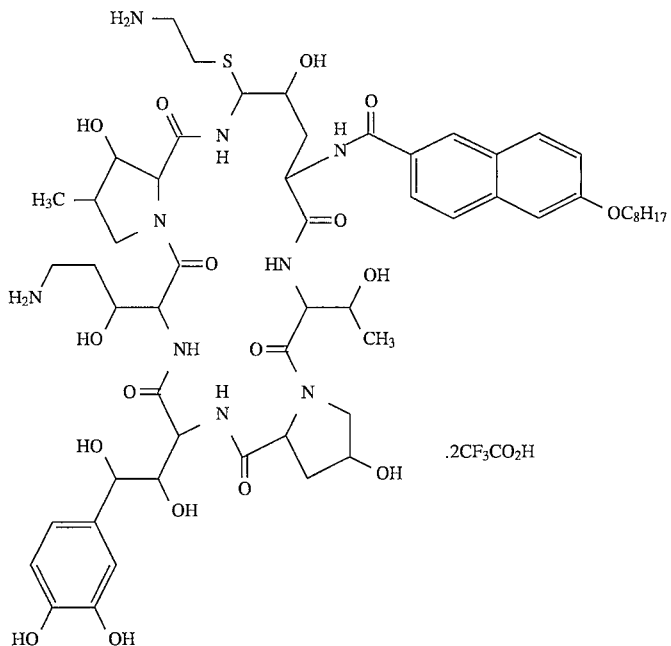

.2CF$_3$CO$_2$H

X-1a-6a

A solution of the amino compound (1.00 mmol) obtained in Example VIII Part B, 2-aminoethanethiol hydrochloride (100 mmol) and (1S)-(+)-10-camphorsulfonic acid (1.00 mmol) in 80 mL of anhydrous N,N-dimethylformamide is stirred at 25° C. for 2–6 days or a period sufficient effect dissapearance of the starting material. The reaction is diluted with 80 milliliters of water and flash chromatographed on "LICHROPREP" (E. Merck) RP 18 (40–63 μm, 30 grams) packed in 10 percent acetonitrile/water. The column is eluted with 10 to 40 percent acetonitrile/water collecting several fractions at each gradient step. The appropriate fractions, as determined by analytical HPLC (Zorbax Rx C18, 40% acetonitrile/water/0.1% trifluoroacetic acid, 210 nm) are concentrated and lyophilized. The residue is further purified by preparative HPLC (ZORBAX C18, 40% acetonitrile/water/0.1%TFA, 210 nm) to obtain the desired compound as a bis-trifluroacetate salt with a molecular weight of 1412.43

EXAMPLE IX

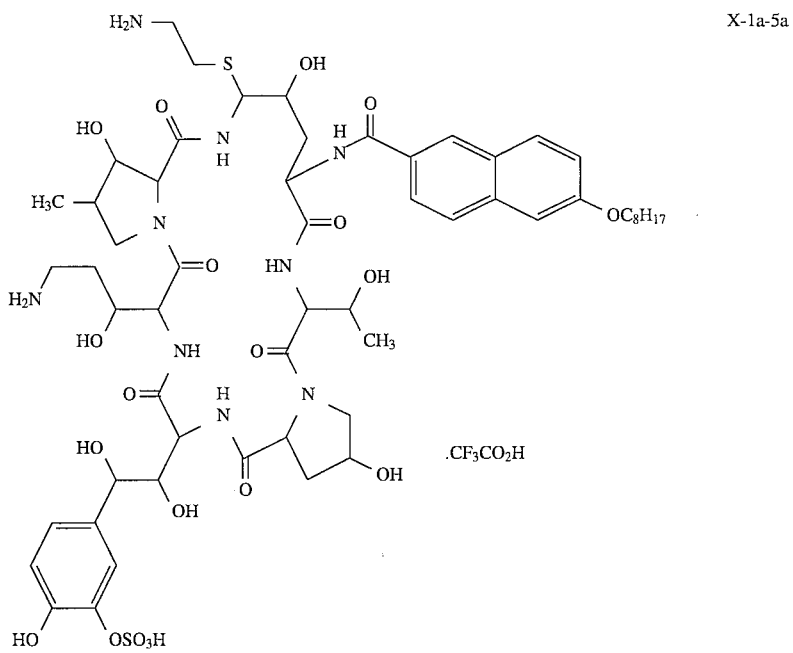

.CF$_3$CO$_2$H

X-1a-5a

A solution of the amino compound (1.00 m_mol) obtained in Example VI Part B, 2-aminoethanethiol hydrochloride (100 mmol) and (1S)-(+)-10-camphorsulfonic acid (1.00 mmol) in 80 mL of anhydrous N,N-dimethylformamide is stirred at 25° C. for 2–6 days or a period sufficient effect dissapearance of the starting material. The reaction is diluted with 80 milliliters of water and flash chromatographed on "LICHROPREP" (E. Merck) RP 18 (40–63 μm, 30 grams)

packed in 10 percent acetonitrile/water/0.5% NH₄H₂PO₄. The column is eluted with 10 to 30 percent acetonitrile/water/0.5% NH₄H₂PO₄ collecting several fractions at each gradient step. The appropriate fractions, as determined by analytical HPLC (Zorbax Rx C18, 40% acetonitrile/water/ 0.1% trifluoroacetic acid, 210 nm) are concentrated and lyophilized. The residue is further purified by preparative HPLC (ZORBAX C18, 30% acetonitrile/water/0.1%TFA, 210 nm) to obtain the desired compound as a trifluoroacetate salt with a molecular weight of 1378.47.

EXAMPLE X

Part B. Oxidation to Sulfone

The thioethers obtained as described in Part A above (0.716 mmol) is dissolved in 30 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 25–35% acetonitrile/water containing 0.1% TFA in 2% step gradients. The product containing fractions as determined by analytical HPLC ("ZORBAX" C18, 30% acetonitrile/water/0.1% TFA, 210 nm) are combined and X-Ia-2a

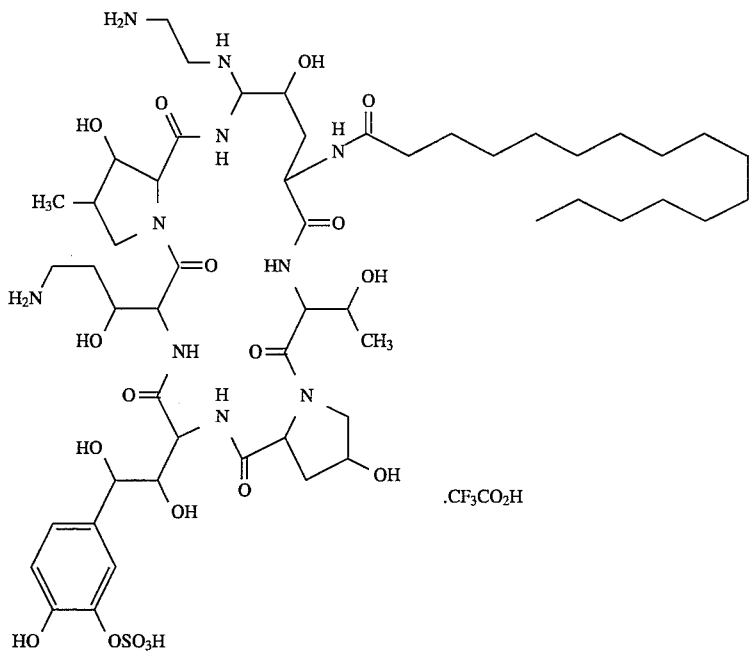

Part A. Preparation of the Intermediate Aminoethylthioether

A solution of the amino compound (1.00 mmol) obtained in Example I Part B, 2-aminoethanethiol hydrochloride (100 mmol) and (1S)-(+)-10-camphorsulfonic acid (1.00 mmol) in 80 mL of anhydrous N,N-dimethylformamide is stirred at 25° C. for 2–6 days or a period sufficient effect dissapearance of the starting material. The reaction is diluted with 80 milliliters of water and flash chromatographed on "LICHROPREP" (E. Merck) RP 18 (40–63 µm, 30 grams) packed in 10 percent acetonitrile/water/0.5% NH₄H₂PO₄. The column is eluted with 10 to 30 percent acetonitrile/water/0.5% NH₄H₂PO₄ collecting several fractions at each gradient step. The appropriate fractions, as determined by analytical HPLC (Zorbax Rx C18, 40% acetonitrile/water/ 0.1% trifluoroacetic acid, 210 nm) are concentrated and lyophilized. The residue is further purified by preparative HPLC (ZORBAX C18, 30% acetonitrile/water/0.1%TFA, 210 nm) to obtain the desired compound as a trifluroacetate salt with a molecular weight of 1334.50.

lyophilized to give the desired product with a molecular weight of 1366.50.

Part C. Displacement of Sulfone with Ethylenediamine

The sulfone mixture (0.15 mmol), obtained as described in Part B above, is dissolved in 3.0 mL of anhydrous DMF and ethylenediamine (1.50 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–25% acetonitrile/water/ 0.1%TFA in 5% step gradients. The appropriate fractions are pooled, frozen and lyophilized to give the desired product with the α-C-5 orn configuration and its β-C-5 orn epimer. The trifluoroacetate salt thus obtained has a molecular weight of 13 17.45.

EXAMPLE XI

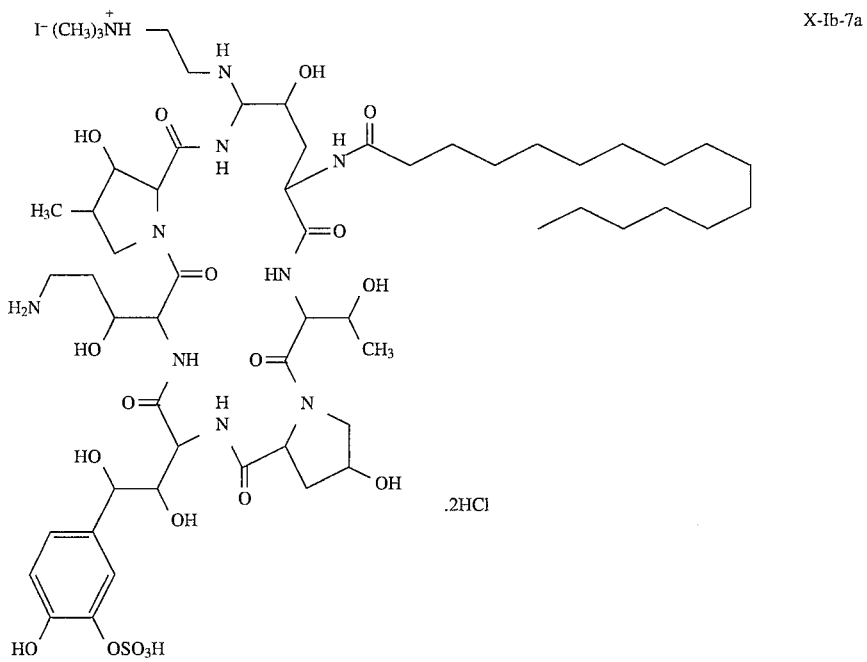

X-Ib-7a

The sulfone mixture (0.3 mmol), obtained as described in Part B of Example X, is dissolved in 6.0 mL of anhydrous DMF and N,N,N-trimethylamomium-2-aminoethane iodide(3.0 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–25% acetonitrile/water/0.1%TFA in 5% step gradients. The appropriate fractions as determined by analytical HPLC ("ZORBAX" RX-C18, 30% acetonitrile/water/0.1% TFA, 210 nm) are pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate is lyophilized to give the desired product as the chloride salt with a molecular weight of 1355.

EXAMPLE XII

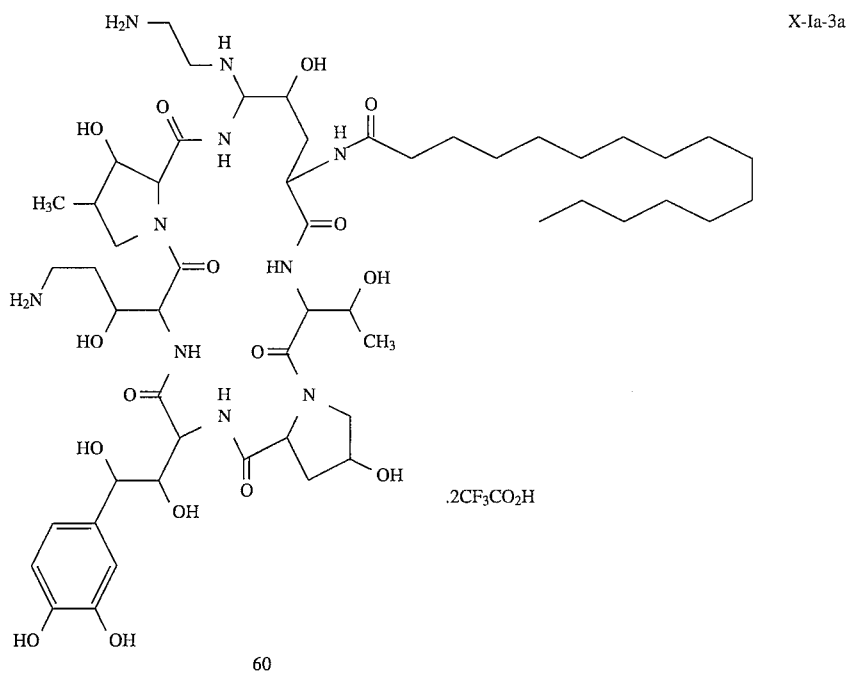

X-Ia-3a

Part A. Preparation of the Intermediate Aminoethylthioether

A solution of the amino compound (1.00 mmol) obtained in Example V Part B, 2-aminoethanethiol hydrochloride (100 mmol) and (1S)-(+)-10-camphorsulfonic acid (1.00 mmol) in 80 mL of anhydrous N,N-dimethylformamide is stirred at 25° C. for 2–6 days or a period sufficient effect dissapearance of the starting material. The reaction is diluted with 80 milliliters of water and flash chromatographed on "LICHROPREP" (E. Merck) RP 18 (40–63 μm, 30 grams) packed in 10 percent acetonitrile/water/0.1% TFA. The column is eluted with 10 to percent acetonitrile/water/0.1% TFA collecting several fractions at each gradient step. The appropriate fractions, as determined by analytical HPLC (Zorbax Rx C18, 40% acetonitrile/water/0.1% trifluoroacetic acid, 210 nm) are concentrated and lyophilized. The residue is further purified by preparative HPLC (ZORBAX C18, 30% acetonitrile/water/0.1%TFA, 210 nm) to obtain the desired compound as a bis-trifluroacetate salt with a molecular weight of 1368.46.

Part B. Oxidation to Sulfone

The thioethers obtained as described in Part A above (0.1 mmol) is dissolved in 5 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 25–35% acetonitrile/water containing 0.1% TFA in 2% step gradients. The product containing fractions as determined by analytical HPLC ("ZORBAX" C18, 30% acetonitrile/water/0.1% TFA, 210 nm) are combined and lyophilized to give the desired product with a molecular weight of 1400.46.

Part C. Displacement of Sulfone with Ethylenediamine

The sulfone mixture (0.05 mmol), obtained as described in Part B above, is dissolved in 3.0 mL of anhydrous DMF and ethylenediamine (0.50 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C 18) flash column chromatography eluting with 10–30% acetonitrile/water/0.1%TFA in 5% step gradients. The appropriate fractions are pooled, frozen and lyophilized to give the desired product with the α-C-5 orn configuration and its β-C-5 orn epimer. The bistrifluoroacetate salt thus obtained has a molecular weight of 1351.41.

EXAMPLE XIII

The sulfone mixture (0.3 mmol), obtained as described in Part B of Example XII, is dissolved in 6.0 mL of anhydrous DMF and N,N-dimethyl-N$^l$-ethyl ethylenediamine (3.0 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–35% acetonitrile/water/0.1%TFA in 5% step gradients. The appropriate fractions as determined by analytical HPLC ("ZORBAX" RX-C18, 45% acetonitrile/water/0.1% TFA, 210 nm) are pooled, frozen and lyophilized to give the desired product with the α-C-5 orn configuration and its β-C-5 orn epimer. The trifluoroacetate salt thus obtained has a molecular weight of 1408.53

EXAMPLE XIV

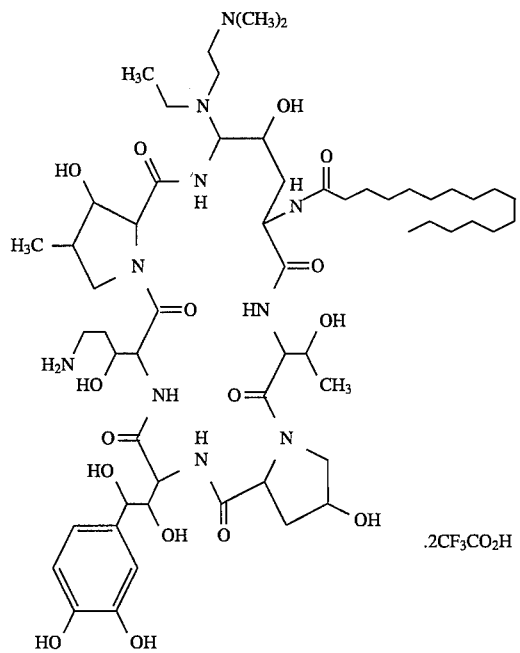

X-Ia-8a

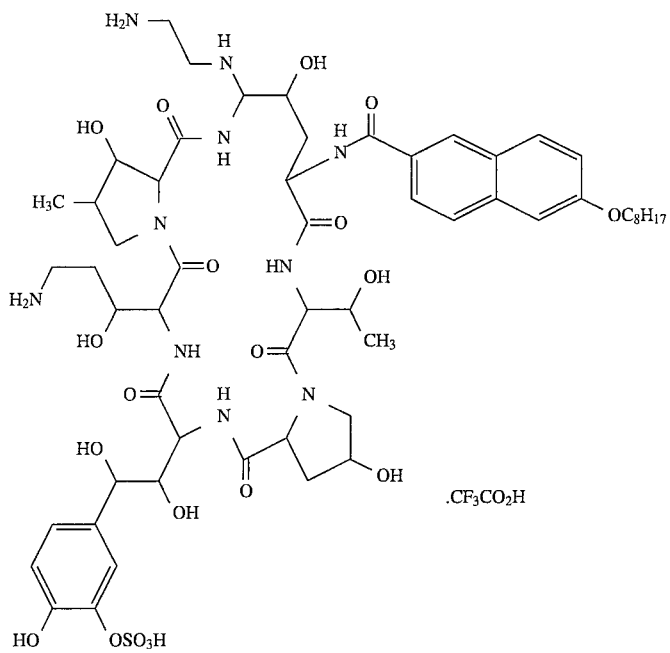

X-Ia-2b

Part A. Preparation of the Sulfone

The thioether obtained as described in Example IX (0.1 mmol) is dissolved in 5 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 25–35 % acetonitrile/water containing 0.1% TFA in 2% step gradients. The product containing fractions as determined by analytical HPLC ("ZORBAX" C18, 30% acetonitrile/water/0.1% TFA, 210 nm) are combined and lyophilized to give the desired product with a molecular weight of 1524.49.

Part B. Displacement of Sulfone with Ethylenediamine

The sulfone mixture (0.05 mmol), obtained as described in Part A above, is dissolved in 3.0 mL of anhydrous DMF and ethylenediamine (0.50 mmol) is added. The mixture is stirred for about 1–12 hours or until analytical HPLC analysis (RP-18, 25% acetonitrile/water/0.1% TFA, 210 nm) shows complete disappearance of the starting sulfone. The mixture is separated by reverse phase (C18) flash column chromatography eluting with 10–30% acetonitrile/water/ 0.1%TFA in 5% step gradients. The appropriate fractions are pooled, frozen and lyophilized to give the desired product with the α-C-5 orn configuration and its β-C-5 orn epimer. The trifluoroacetate salt thus obtained has a molecular weight of 1475.45.

EXAMPLE XV

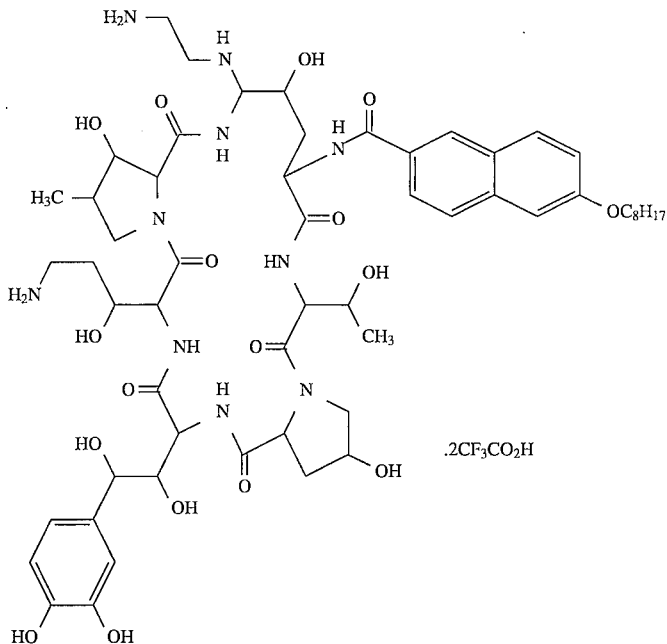

X-Ia-3b

Part A. Preparation of the Sulfone

The thioether obtained as described in Example VIII (0.1 mmol) is dissolved in 5 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 25–45% acetonitrile/water containing 0.1% TFA in 2% step gradients. The product containing fractions as determined by analytical HPLC ("ZORBAX" C18, 30% acetonitrile/water/0.1% TFA, 210 nm) are combined and lyophilized to give the desired product with a molecular weight of 1444.43.

Part B. Displacement of Sulfone with Ethylenediamine

The sulfone mixture (0.05 mmol), obtained as described in Part A above, is dissolved in 3.0 mL of anhydrous DMF and ethylenediamine (0.50 mmol) is added. The mixture is stirred for about 1–12 hours or until analytical HPLC analysis (RP-18, 35% acetonitrile/water/0.1% TFA, 210 nm) shows complete disappearance of the starting sulfone. The mixture is separated by reverse phase (C18) flash column chromatography eluting with 10–40% acetonitrile/water/0.1%TFA in 5% step gradients. The appropriate fractions are pooled, frozen and lyophilized to give the desired product with the α-C-5 orn configuration and its β-C-5 orn epimer. The bistrifluoroacetate salt thus obtained has a molecular weight of 1395.38.

EXAMPLE XVI

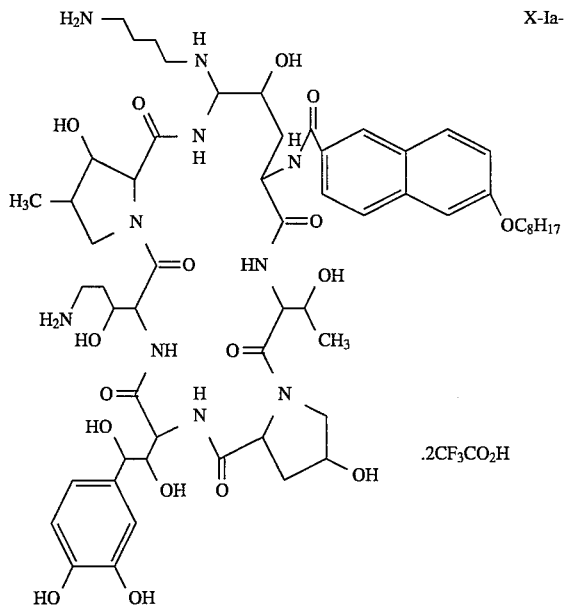

In an analogous fashion to Example XV but using 1,4-diamino butane in place of ethylenediamine, the corresponding adduct as the trifluoroacetate salt with a molecular weight of 1423.44 may be obtained.

The following examples illustrate representative compositions containing the compounds of the invention.

EXAMPLE A 1000 hard gelatin capsules each containing 500 mg of Compound 10 are prepared from the following formulation:

| Compound | Grams |
|---|---|
| Compound 10 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE B

An aerosol composition may be prepared having the following formulation:

|  | Per Canister |
|---|---|
| Compound 10 | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE C 250 milliliters of an injectible solution may be prepared by conventional procedures having the following formulation:

| Dextrose | 12.5 g |
|---|---|
| Water | 250 ml |
| Compound 10 | 400 mg |

The ingredients are blended and thereafter sterilized for use.

Preparation of Starting Materials:

The starting materials for the compounds are natural products or derivatives of natural products.

These compounds are described in European Patent Applns. 0,431,350 and 0,462,531 to Fujisawa Pharmaceutical Co.

Starting materials in which $R^I$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experentia 34, 1670 (1978) or U.S. Pat. No. 4,293,482, and thereafter recovering the deacylated cyclopeptide, and acylating the deacylated cyclopeptide by mixing together with an appropriate active ester $R^ICOX$ to obtain Compound E with the desired acyl group using conventional procedures. Methods are also described in U.S. Pat. No. 4,287,120 and 4,293,489.

What is claimed is:

1. A compound selected from the group consisting of

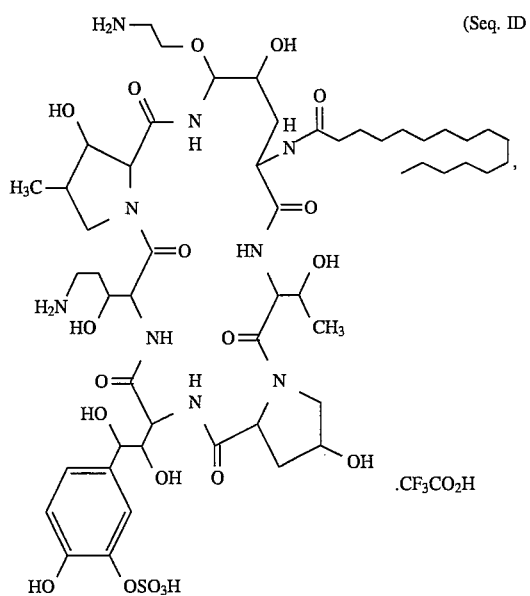
(Seq. ID No. 1)
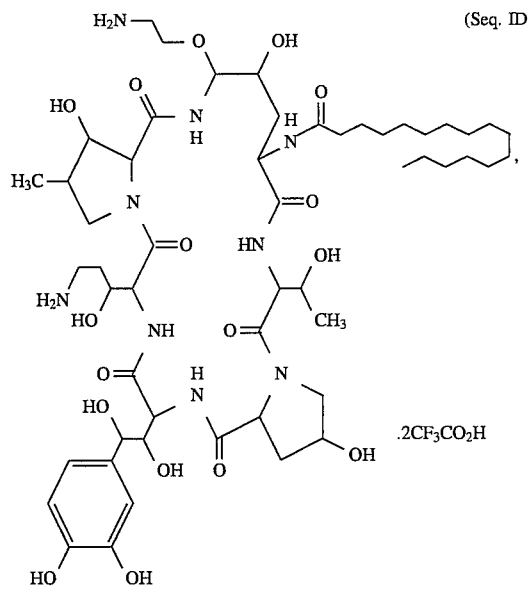
(Seq. ID No. 4)
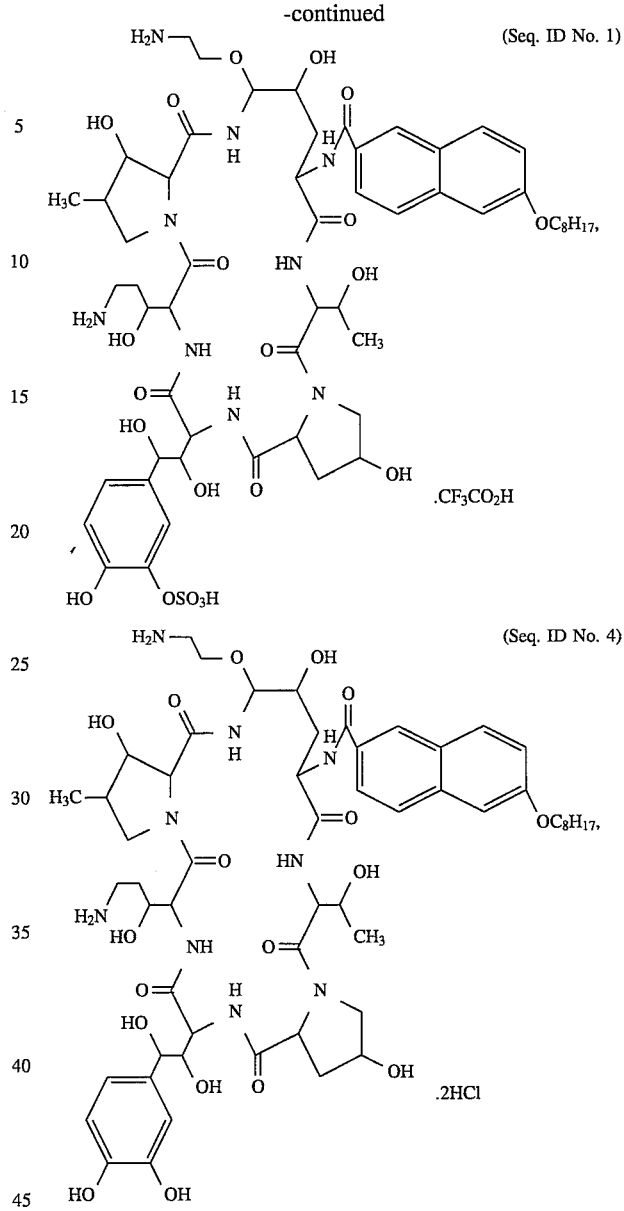

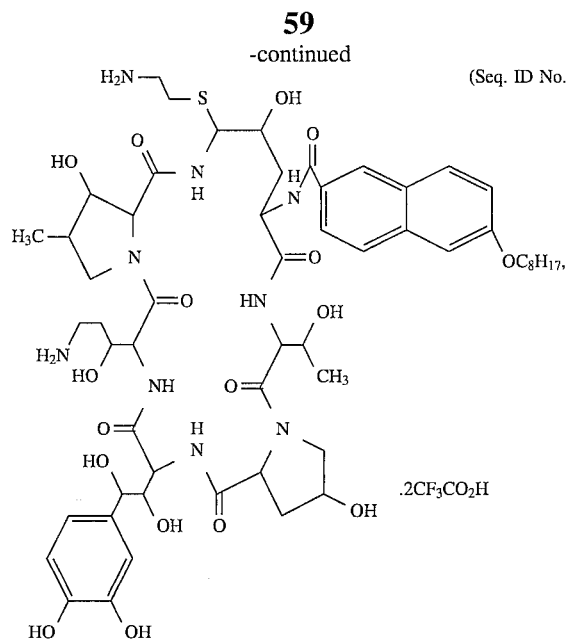
(Seq. ID No. 4)
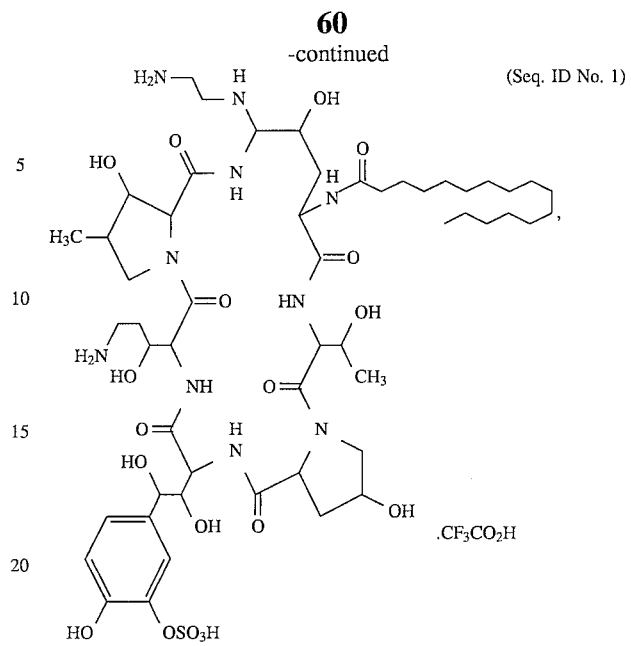
(Seq. ID No. 1)
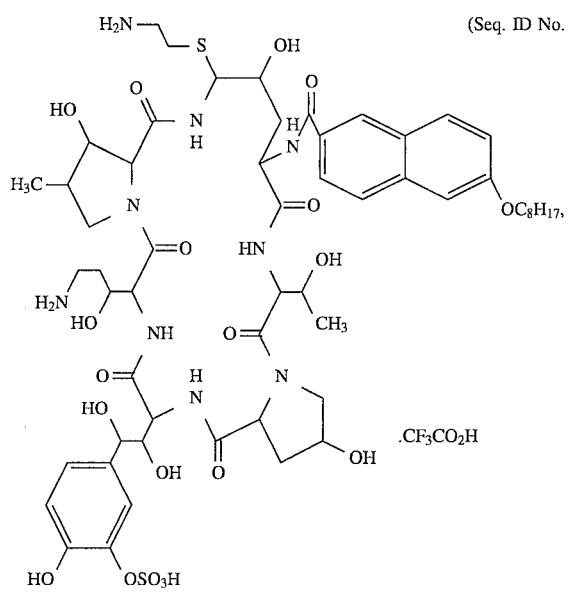
(Seq. ID No. 1)
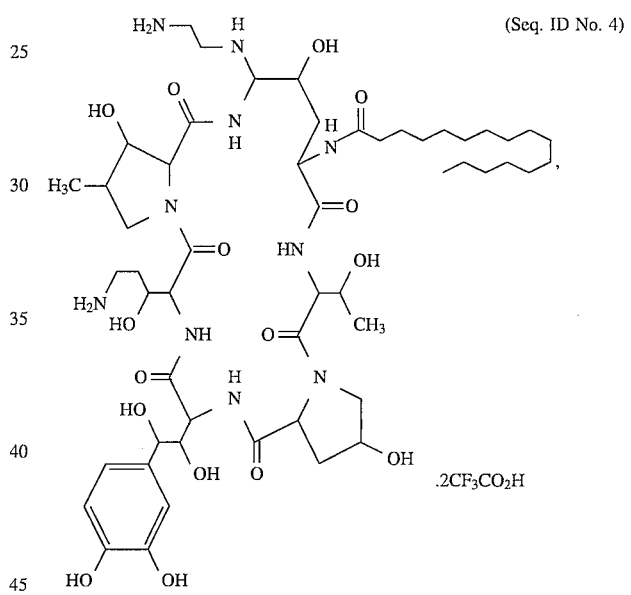
(Seq. ID No. 4)

-continued

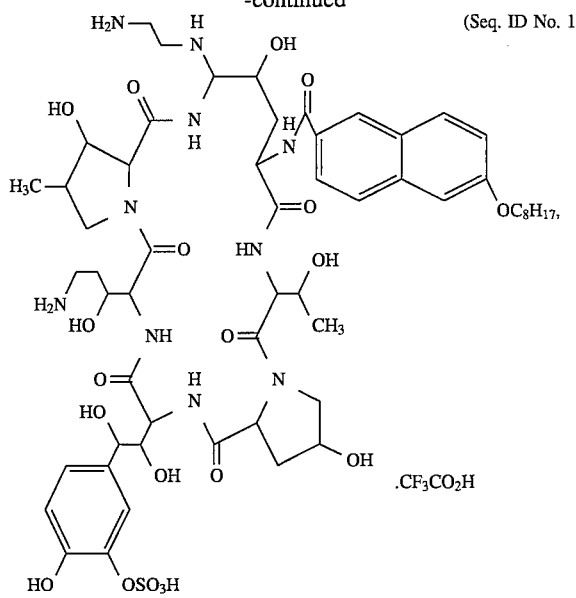
(Seq. ID No. 1)

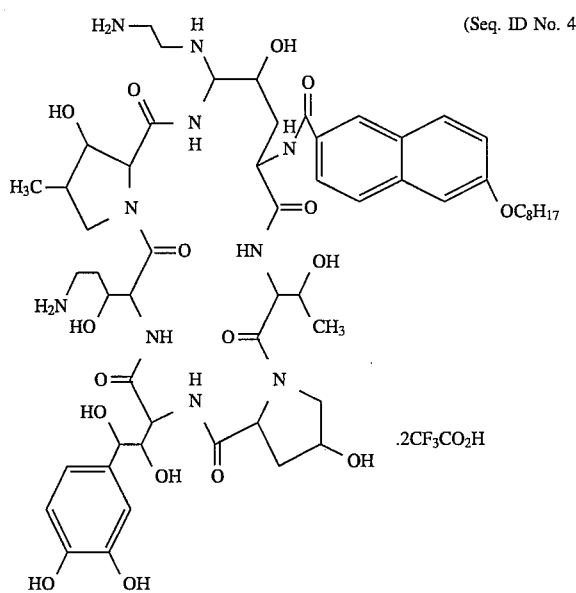
(Seq. ID No. 4)

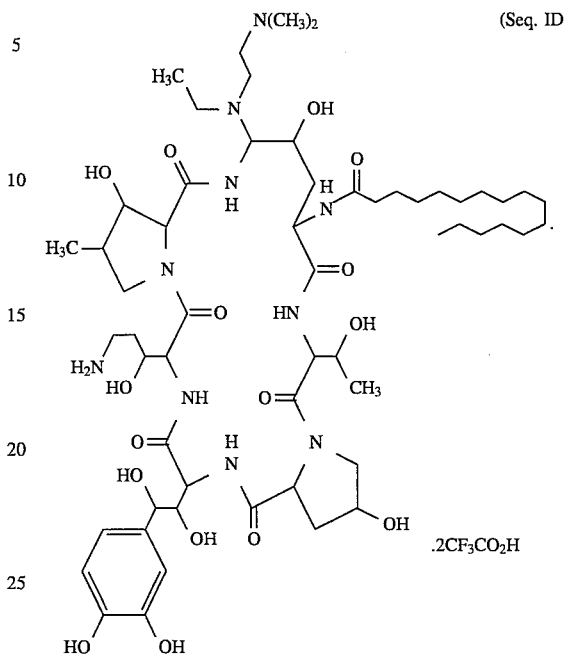
(Seq. ID No. 4)

2. A pharmaceutical composition which comprises a therapeutic amount of a compound of claim 1 in a pharmaceutically acceptable carrier.

3. A composition according to claim 2 in unit dosage form wherein the compound is present in an amount of 10 milligrams to 200 milligrams.

4. A method for treating fungal infections in a mammalian patient in need of said treatment which comprises administering an antifungal effective mount of a compound of claim 1.

5. A method for treating *Pneumocystis carinii* infections in a mammalian patient in need of said treatment which comprises administering an anti-Pneumocystis effective amount of a Compound of claim 1.

* * * * *